(12) United States Patent
Gebert-Schwarzwalder et al.

(10) Patent No.: US 9,364,408 B2
(45) Date of Patent: *Jun. 14, 2016

(54) HAIR DYE AGENT COMPRISING AMINOPYRIMIDINE DERIVATIVES

(71) Applicant: Henkel AG & Co. KGaA, Duesseldorf (DE)

(72) Inventors: Antje Gebert-Schwarzwalder, Duesseldorf (DE); Helmut Giesa, Meerbusch (DE); Annika Koenen, Grevenbroich (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/682,389

(22) Filed: Apr. 9, 2015

(65) Prior Publication Data

US 2015/0209258 A1    Jul. 30, 2015

Related U.S. Application Data

(63) Continuation of application No. PCT/EP2013/070432, filed on Oct. 1, 2013.

(30) Foreign Application Priority Data

Oct. 10, 2012    (DE) .......................... 10 2012 218 459

(51) Int. Cl.
*A61Q 5/10* (2006.01)
*A61K 8/49* (2006.01)
*C07D 239/50* (2006.01)

(52) U.S. Cl.
CPC ............. *A61K 8/4953* (2013.01); *A61Q 5/10* (2013.01); *C07D 239/50* (2013.01); *A61K 2800/4324* (2013.01)

(58) Field of Classification Search
CPC ....... A61Q 5/10; A61K 8/4953; A61K 8/415; A61K 8/4926; A61K 8/347; C09B 62/205

USPC ............................................................ 8/405
See application file for complete search history.

(56) References Cited

U.S. PATENT DOCUMENTS 4,046,503 A * 9/1977 Kubersky ................. A61Q 5/10
8/409

FOREIGN PATENT DOCUMENTS

WO    2006/029712 A1    3/2006

OTHER PUBLICATIONS

STIC Search Report dated May 15, 2015.*
PCT International Search Report (PCT/EP2013/070432) dated Apr. 2, 2014.
Boyle et al, "Synthesis and Properties of 7-Alkoxyfurazano[3,4-d]pyrimidines and Their Use in the Preparation of 4-Alkoxypteridines and N3-Substituted Pterines", XP008041325, The Journal of Organic Chemistry, American Chemical Society, vol. 50, No. 25, pp. 5127-5132, 1985.

* cited by examiner

*Primary Examiner* — Eisa Elhilo
(74) *Attorney, Agent, or Firm* — P. Scott Smith

(57) ABSTRACT

The present application relates to agents for dyeing keratin fibers, in particular human hair, the agent including a cosmetic carrier and at least a compound of formula (I)

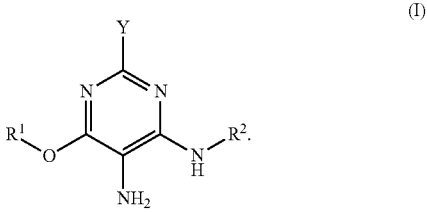

16 Claims, No Drawings

HAIR DYE AGENT COMPRISING AMINOPYRIMIDINE DERIVATIVES

FIELD OF THE INVENTION

The present invention generally relates to an agent for changing the color of keratin-containing fibers, particularly human hair, which agent contains certain substituted aminopyrimidine derivatives.

The invention further relates to the use of the substituted aminopyrimidine derivatives in dye agents to improve the dyeing results, and to certain substituted aminopyrimidine derivatives.

BACKGROUND OF THE INVENTION

The changing of the shape and the color of hair is an important field of modern cosmetics. The consumer uses color-changing agents for the stylish coloring of hairstyles or for the concealment of gray or white hair with stylish or natural shades of color.

A person skilled in the art knows various systems for providing color-changing cosmetic agents, in particular for the skin or keratin-containing fibers such as human hair, depending on the requirements for the coloring or color change.

For permanent, intense colorings having corresponding fastness properties, so-called oxidation dye agents are used. Such dye agents usually include oxidation dye intermediates, so-called developer components and coupler components. The developer components form the actual dyes under the influence of oxidants or atmospheric oxygen, among each other or by coupling with one or more coupler components. The oxidation dye agents are distinguished by intense, excellent, long-lasting dyeing results. For natural-looking colorings, a mixture of a larger number of oxidation dye intermediates can be used, wherein in many cases direct dyes are additionally used for nuancing.

Oxidative hair dye agents in particular often have disadvantages despite their advantageous dyeing properties for the user, and therefore there is a constant demand for development for oxidation dye intermediates.

In the search for oxidation dye intermediates having a good compatibility profile, many compounds were researched, which, however, often suffered from usage-related problems, particularly a lack of gray coverage capability. In addition, despite already highly developed dyeing systems, there is a still a need for dyeing systems that achieve excellent brightness and intensity of the colorings but at the same time are long-lasting, have very good fastness properties, and have excellent homogeneity.

Particularly in the field of red and blue colorings, there is a need for improvement.

Many known dyeing systems by means of which red and blue color nuances can be achieved do not have satisfactory wash fastness and do not have sufficient leveling capability.

In the attainment of blue color nuances, the browning of the blue shades is disadvantageous, which could sometimes be observed when conventional triaminopyrimidine was used as a developer component.

Therefore, the problem to be addressed by the present invention is that of decreasing the aforementioned disadvantages of oxidative hair dye agents. The dye agents should produce intense colorings having high colorfulness and having good resistance to external influences, particularly having good light fastness and wash fastness, that do not suffer any color fading or color shifting even after the hair has been shampooed several times. Furthermore, the colorings should be as little selective as possible, i.e., should achieve dyeing results that are as even and uniform as possible on hair pretreated differently. In addition, the dye agents should have a toxicologically advantageous profile.

A further problem to be addressed by the invention is that of developing oxidation dye intermediates by means of which in particular red and/or blue color nuances having excellent wash fastness and good leveling capability can be achieved. In particular, the browning of blue shades should be avoided.

Finally, it is desirable to achieve the greatest possible nuancing of the individual shades of color.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An agent for dyeing keratin fibers, particularly human hair, characterized in that the agent includes a cosmetic carrier and at least one compound of formula (I) and/or one physiologically acceptable salt of a compound of formula (I)

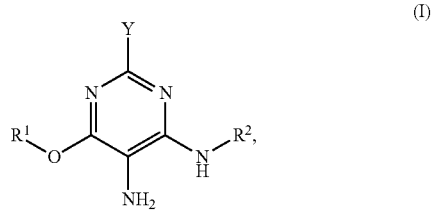

(I)

in which $R^1$, $R^2$ stand, independently of each other, for a hydrogen atom, a $C_1$-$C_8$ alkyl group, a $C_2$-$C_6$ alkenyl group, a $C_1$-$C_6$ hydroxyalkyl group, a $C_2$-$C_8$ polyhydroxyalkyl group, a $C_1$-$C_6$ alkoxy group, a $C_1$-$C_6$ alkoxy $C_1$-$C_6$ hydroxyalkyl group, a $C_1$-$C_6$ alkoxy $C_2$-$C_6$ alkyl group, a $C_1$-$C_6$ polyalkoxy group, an amino $C_2$-$C_6$ alkyl group, wherein the amino group can be substituted with one or two groups X, a $C_1$-$C_6$ alkylamino $C_2$-$C_6$ alkyl group, a $C_1$-$C_6$ alkylamino ($C_1$-$C_6$) alkoxy group, a nitro ($C_1$-$C_6$) alkyl group, a $C_1$-$C_6$ cyanoalkyl group, a $C_1$-$C_6$ alkylamido ($C_1$-$C_6$) alkyl group, wherein the amide function can be substituted with one or two groups X, an aryl group, or a halogen ($C_1$-$C_6$) alkyl group, wherein the halogen can be fluorine, chlorine, bromine, or iodine; and Y stands for an $NH_2$ or OH group, with the proviso that, if $R^1$ stands for a $C_1$-$C_4$ alkyl group, $R^2$ does not stand for hydrogen, a $C_1$-$C_4$ alkyl group, or an aryl group.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It was found that certain alkoxylated aminopyrimidine derivatives as oxidation dye intermediates are excellently suited for dyeing keratin-containing fibers. They produce colorations having good fastness properties, high color intensity, excellent brilliance, and excellent gray coverage.

Triaminoalkoxypyrimidine derivatives as developer components in oxidative hair dye agents are known from the laid-open application DE 2516117.

Alkoxylated aminopyrimidine derivatives according to formula (I) below as oxidation dye intermediates have not been known until now.

Therefore, first subject matter of the invention is an agent for dyeing keratin fibers, particularly human hair, which agent is characterized in that it includes a cosmetic carrier and at least one compound of formula (I) and/or one physiologically acceptable salt of a compound of formula (I),

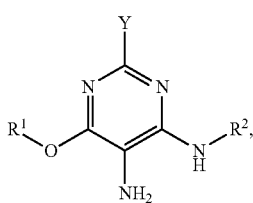
(I)

in which
$R^1$, $R^2$ stand, independently of each other, for a hydrogen atom, a $C_1$-$C_8$ alkyl group, a $C_2$-$C_6$ alkenyl group, a $C_1$-$C_6$ hydroxyalkyl group, a $C_2$-$C_8$ polyhydroxyalkyl group, a $C_1$-$C_6$ alkoxy group, a $C_1$-$C_6$ alkoxy $C_1$-$C_6$ hydroxyalkyl group, a $C_1$-$C_6$ alkoxy $C_2$-$C_6$ alkyl group, a $C_1$-$C_6$ polyalkoxy group, an amino $C_2$-$C_6$ alkyl group, wherein the amino group can be substituted with one or two groups X, a $C_1$-$C_6$ alkylamino $C_1$-$C_6$ alkyl group, a $C_1$-$C_6$ alkylamino ($C_1$-$C_6$) alkoxy group, a nitro ($C_1$-$C_6$) alkyl group, a $C_1$-$C_6$ cyanoalkyl group, a $C_1$-$C_6$ alkylamido ($C_1$-$C_6$) alkyl group, wherein the amide function can be substituted with one or two groups X, an aryl group, or a halogen ($C_1$-$C_6$) alkyl group, wherein the halogen can be fluorine, chlorine, bromine, or iodine, Y stands for an $NH_2$ or OH group,
with the proviso that, if $R^1$ stands for a $C_1$-$C_4$ alkyl group, $R^2$ does not stand for hydrogen, a $C_1$-$C_4$ alkyl group, or an aryl group.

By "keratin fibers", wool, furs, feathers, and particularly human hair should be understood. In principle, however, the dye agents according to the invention can also be used to dye other natural fibers, such as cotton, jute, sisal, linen, or silk, or modified natural fibers, such as regenerated cellulose, nitro, alkyl or hydroxyalkyl or acetyl cellulose.

The agents according to the invention include the compounds of formula (I) in a cosmetic carrier, preferably in a suitable aqueous, alcoholic, or aqueous-alcoholic carrier. For the purpose of hair dyeing, such carriers are, for example, creams, emulsions, gels, or surfactant-containing foaming solutions, such as shampoos, foam aerosols, foam formulations, or other preparations that are suitable for application to hair. However, it is also conceivable to integrate the compounds according to formula (I) into a powdery formulation or a formulation in the tablet form.

By aqueous-alcoholic solutions, within the meaning of the present invention, aqueous solutions containing 3 to 70 wt % of a $C_1$-$C_4$ alcohol, in particular ethanol or isopropanol, should be understood. The agents according to the invention can additionally include further organic solvents, such as methoxybutanol, benzyl alcohol, ethyl diglycol, or 1,2-propylene glycol. All water-soluble organic solvents are preferred.

Examples of a $C_1$-$C_8$ alkyl group are the groups methyl, ethyl, propyl, isopropyl, n-butyl, s-butyl, and t-butyl, n-pentyl, i-pentyl, i-hexyl, n-hexyl, n-heptyl, i-heptyl, i-octyl, and n-octyl. Examples of a $C_2$-$C_6$ alkenyl group are vinyl, allyl, but-2-enyl, but-3-enyl, and isobutenyl; preferred $C_2$-$C_6$ alkenyl residues are vinyl and allyl. Preferred examples of a $C_1$-$C_6$ hydroxyalkyl group are a hydroxymethyl, a 2-hydroxyethyl, a 2-hydroxypropyl, a 3-hydroxypropyl, a 4-hydroxybutyl, a 5-hydroxypentyl, and a 6-hydroxyhexyl group; a 2-hydroxyethyl group is especially preferred. $C_1$-$C_6$ alkoxy groups preferred according to the invention are the methoxy, ethoxy, or propoxy group. Examples of a $C_2$-$C_8$ polyhydroxyalkyl group are the 2,3-dihydroxypropyl group, the 3,4-dihydroxybutyl group, and the 2,4-dihydroxybutyl group. The 2-methoxyethyl group, the 2-ethoxyethyl group, the 3-methoxypropyl group, and the 3-ethoxypropyl group are examples of a $C_1$-$C_6$ alkoxy $C_2$-$C_6$ alkyl group; the 2-methoxyethyl group and the 2-ethoxyethyl group are preferred. Preferred examples of a $C_1$-$C_6$ alkoxy $C_2$-$C_6$ hydroxyalkyl group are the groups methoxymethanol, methoxyethanol, methoxypropan-1-ol, methoxybutan-1-ol, 2-ethoxymethanol, 2-ethoxyethanol, 2-ethoxypropan-1-ol, or 4-ethoxybutan-1-ol. Examples of $C_1$-$C_6$ polyalkoxy groups preferred according to the invention are the (methoxymethoxy)methoxy group, the 2-(2-methoxyethoxyl)ethoxy group, the 3-(3-methoxypropoxy)propoxy group, the (ethoxymethoxy)methoxy group, the 2-(2-ethoxyethoxy)ethoxy group, and the 3-(3-ethoxypropoxy)propoxy group. Examples of an amino $C_2$-$C_6$ alkyl group are the methylamino, the ethylamino, and the propylamino group. Examples of a $C_1$-$C_6$ alkylamino ($C_1$-$C_6$) alkoxy group are a [(methoxymethyl)amino]methyl group, a 2-[(2-methoxyethyl)amino]ethyl group, a [(2-ethoxyethyl)amino]ethyl group, or a 3-[(3-methoxypropyl)amino]propyl group. Preferred examples of $C_1$-$C_6$ alkylamino ($C_1$-$C_6$) alkyl groups are the (methylamino)methyl group, the (methylamino)ethyl group, the (methylamino)propyl group, the (methylamino)butyl group, the (ethylamino)methyl group, the (ethylamino)ethyl group, or the (ethylamino)propyl group. Preferred examples of a nitro ($C_1$-$C_6$) alkyl group are the nitromethyl, the 2-nitroethyl, the 3-nitropropyl, and the 4-nitrobutyl group. Preferred examples of a cyano $C_1$-$C_6$ alkyl group are a cyanomethyl group and a 2-cyanoethyl group. Examples of a $C_1$-$C_6$ alkylamido $C_1$-$C_6$ alkyl group are the N-methyl-2-acetamide group, the N,N-dimethyl-2-acetamide group, the N-ethyl-2-acetamide group, the N,N-diethyl-2-acetamide group, the N-Methyl-3-propanamide group, and the N,N-diethyl-3-propanamide group. Preferred examples of aryl groups are phenyl, toluyl, and benzyl. Preferred halogen ($C_1$-$C_6$) alkyl groups are the 2-chloroethyl group, the 3-chloropropyl group, the 2-bromoethyl group, and the 3-bromopropyl group.

In the course of the work leading to this invention, it emerged that it is particularly advantageous if the groups $R^1$ and $R^2$ stand, independently of each other, for a hydrogen atom, a $C_1$-$C_6$ alkyl group, an aryl group, a $C_1$-$C_6$ hydroxyalkyl group, a $C_1$-$C_6$ alkoxy group, a $C_1$-$C_6$ alkoxy $C_1$-$C_6$ hydroxyalkyl group, a $C_1$-$C_6$ polyalkoxy group, an amino $C_2$-$C_6$ alkyl group, a $C_1$-$C_6$ alkylamino $C_2$-$C_6$ alkyl group, or a $C_1$-$C_6$ alkylamino ($C_1$-$C_6$) alkoxy group, with the proviso that, if $R^1$ stands for a $C_1$-$C_4$ alkyl group, $R^2$ does not stand for hydrogen, a $C_1$-$C_4$ alkyl group, or an aryl group.

Especially preferably, the group $R^1$ stands for a $C_1$-$C_6$ hydroxyalkyl group, a $C_1$-$C_6$ polyalkoxy group, a $C_1$-$C_6$ alkoxy $C_1$-$C_6$ hydroxy group, a $C_1$-$C_6$ alkylamino $C_2$-$C_6$ alkyl group, a $C_1$-$C_6$ alkylamino $C_2$-$C_6$ alkoxy group, or an aryl group, and $R^2$ stands for hydrogen, a $C_1$-$C_6$ alkyl group, or an aryl group.

If Y stands for an $NH_2$ group, this is likewise especially favorable for the solution of the problem addressed by the invention and therefore is preferred.

In an especially preferred embodiment, the compounds according to formula (I) are derivatives of 6-hydroxy-triaminopyrimidine and thus are amino compounds. The known acid addition salts can be produced from these in a typical manner. Therefore, all statements of this document and accordingly the claimed scope of protection relate both to the compounds present in a free form and to their physiologically acceptable salts of organic or inorganic acids. Examples of such salts are the hydrochlorides, the hydrobromides, the sulfates, the phosphates, the acetates, the propionates, the citrates, and the lactates. The hydrochlorides and the sulfates are especially preferred. Exceptionally preferred according to the invention are the monohydrochlorides, the dihydrochlorides, and the trihydrochlorides.

A further preferred embodiment of the first subject matter of the invention is characterized in that the agent includes at least one compound according to formula (I), which is selected from:

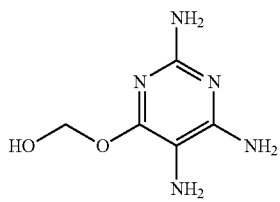

[(2,5,6-triaminopyrimidin-4-yl)oxy]methanol

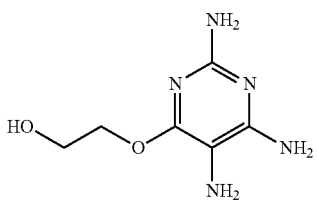

[(2,5,6-triaminopyrimidin-4-yl)oxy]ethanol

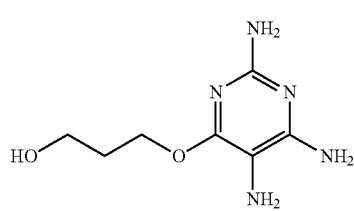

[(2,5,6-triaminopyrimidin-4-yl)oxy]propanol

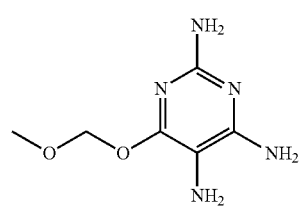

6-(methoxymethoxy)pyrimidine-2,4,5-triamine

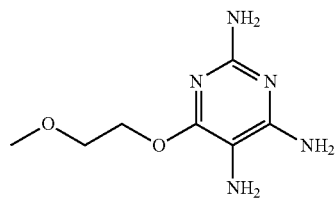

6-(2-methoxyethoxy)pyrimidine-2,4,5-triamine

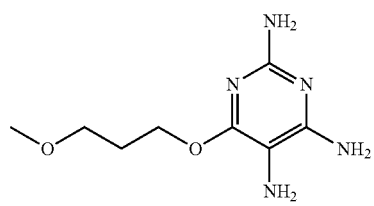

6-(3-methoxypropoxy)pyrimidine-2,4,5-triamine

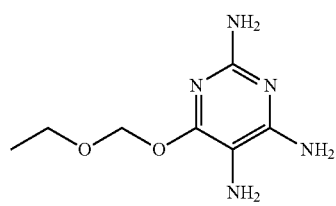

6-(ethoxymethoxy)pyrimidine-2,4,5-triamine

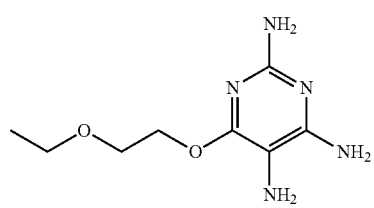

6-(2-ethoxyethoxy)pyrimidine-2,4,5-triamine

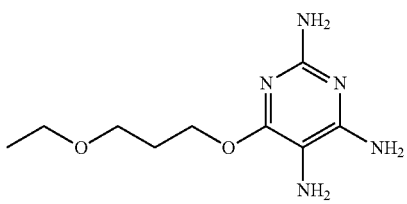

6-(3-ethoxypropoxy)pyrimidine-2,4,5-triamine

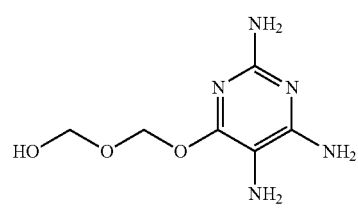

{[(2,5,6-triaminopyrimidin-4-yl)oxy]methoxy}methanol

-continued

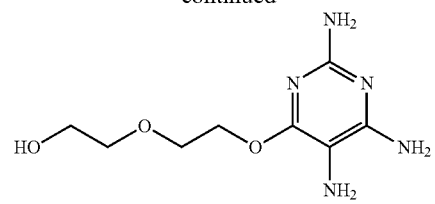

{[(2,5,6-triaminopyrimidin-4-yl)oxy]ethoxy}ethanol

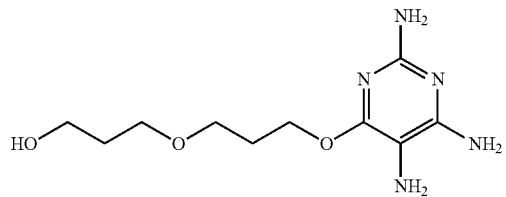

{[(2,5,6-triaminopyrimidin-4-yl)oxy]propoxy}propanol

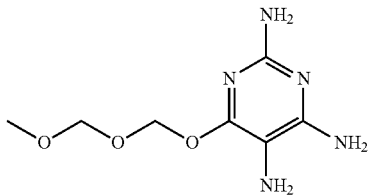

6-[(methoxymethoxy)methoxy]pyrimidine-2,4,5-triamine

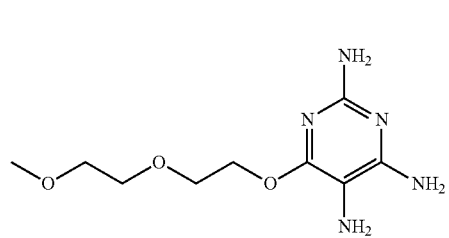

6-[2-(2-methoxyethoxy)ethoxy]pyrimidine-2,4,5-triamine

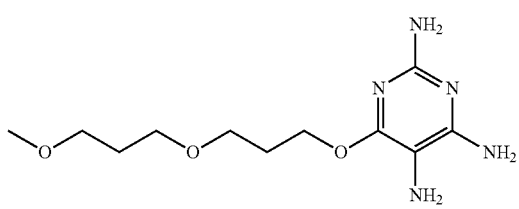

6-[3-(3-methoxypropoxy)propoxy]pyrimidine-2,4,5-triamine

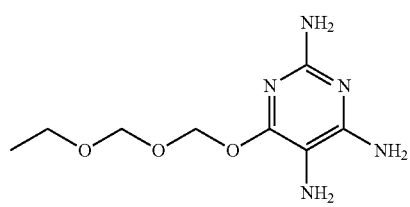

6-[(ethoxymethoxy)methoxy]pyrimidine-2,4,5-triamine

-continued

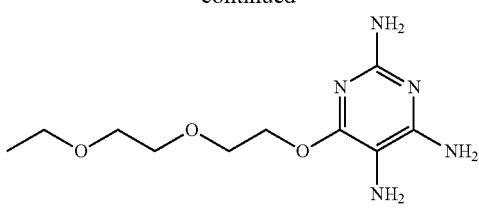

6-[2-(2-ethoxyethoxy)ethoxy]pyrimidine-2,4,5-triamine

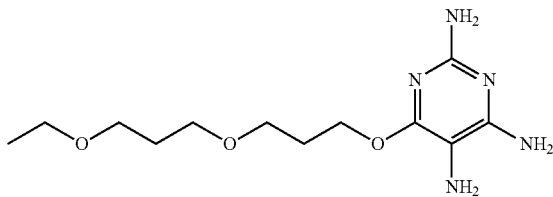

6-[3-(3-ethoxypropoxy)propoxy]pyrimidine-2,4,5-triamine

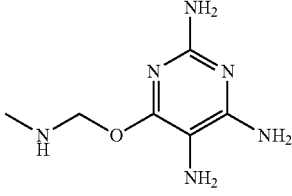

6-[(methylamino)methoxy]pyrimidine-2,4,5-triamine

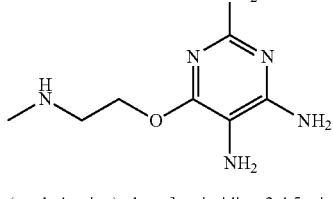

6-[2-(methylamino)ethoxy]pyrimidine-2,4,5-triamine

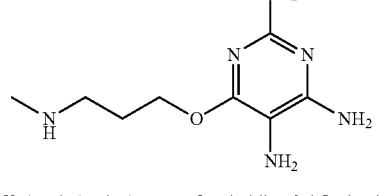

6-[3-(methylamino)propoxy]pyrimidine-2,4,5-triamine

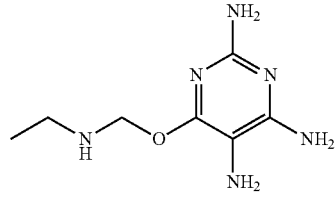

6-[(ethylamino)methoxy]pyrimidine-2,4,5-triamine

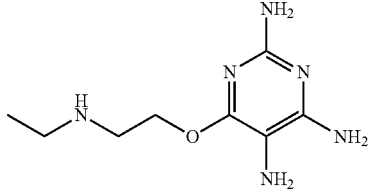

6-[2-(ethylamino)ethoxy]pyrimidine-2,4,5-triamine

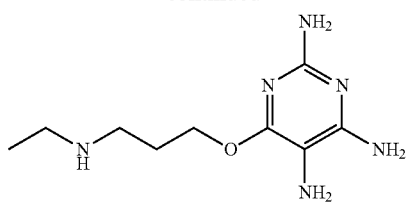

6-[2-(ethylamino)propoxy]pyrimidine-2,4,5-triamine

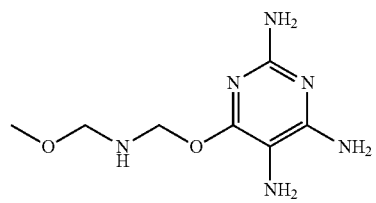

6-{[(methoxymethyl)amino]methoxy}pyrimidine-2,4,5-triamine

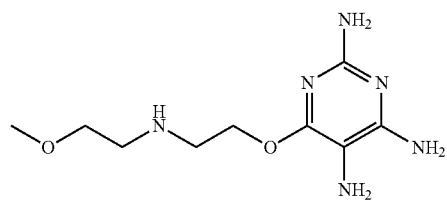

6-{2-[(2-methoxyethyl)amino]ethoxy}pyrimidine-2,4,5-triamine

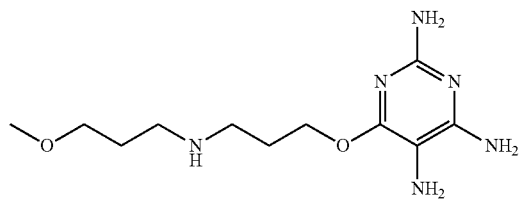

6-{3-[(3-methoxypropyl)amino]propoxy}pyrimidine-2,4,5-triamine

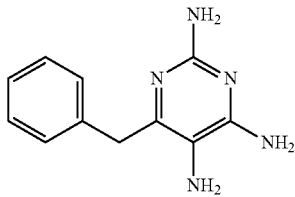

6-phenoxypyrimidine-2,4,5-triamine

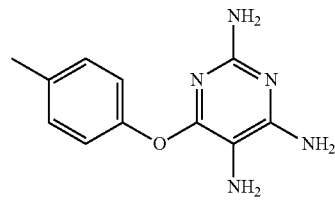

6-(4-methylphenoxy)pyrimidine-2,4,5-triamine

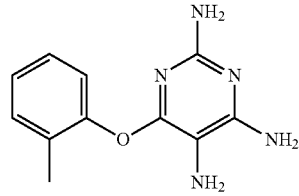

6-(2-methylphenoxy)pyrimidine-2,4,5-triamine

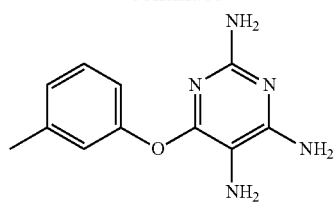

6-(3-methylphenoxy)pyrimidine-2,4,5-triamine

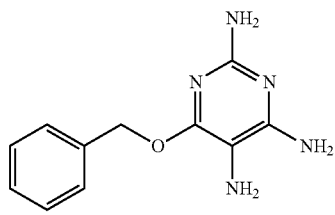

6-benzyloxypyrimidine-2,4,5-triamine

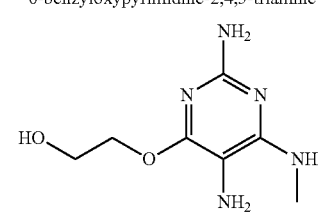

2-{[2,5-diamino-6-(methylamino)pyrimidin-4-yl]oxy}ethanol

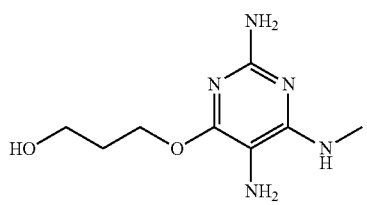

[2,5-diamino-6-(methylamino)pyrimidin-4-yl]oxy]propanol

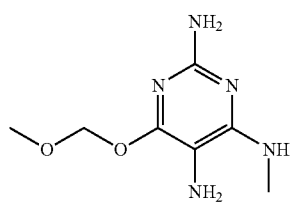

6-(methoxymethoxy)-$N^4$-methylpyrimidine-2,4,5-triamine

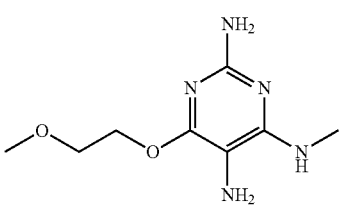

6-(2-methoxyethoxy)-$N^4$-methylpyrimidine-2,4,5-triamine

-continued

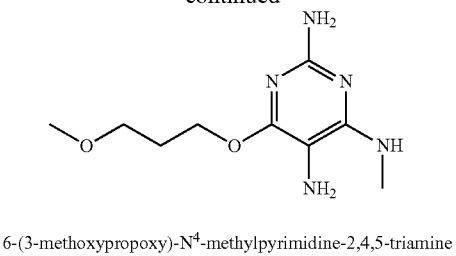

6-(3-methoxypropoxy)-N⁴-methylpyrimidine-2,4,5-triamine

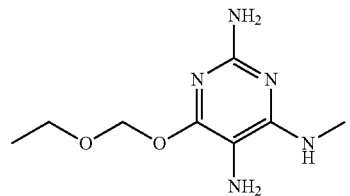

6-(ethoxymethoxy)-N⁴-methylpyrimidine-2,4,5-triamine

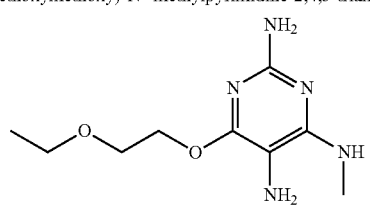

6-(2-ethoxyethoxy)-N⁴-methylpyrimidine-2,4,5-triamine

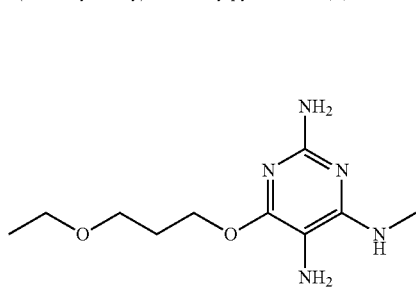

6-(3-ethoxypropoxy)-N⁴-methylpyrimidine-2,4,5-triamine

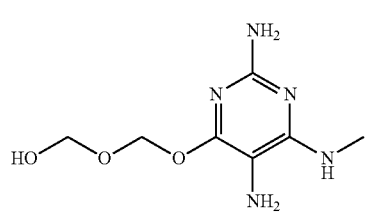

({[2,5-diamino-6-(methylamino)pyrimidin-4-yl]oxy}methoxy)methanol

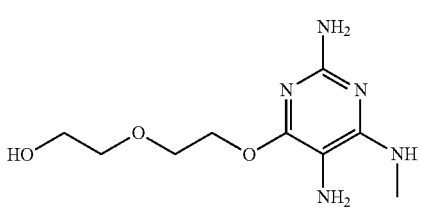

2-(2-{[2,5-diamino-6-methylamino)pyrimidin-4-yl]oxy}ethoxy)ethanol

-continued

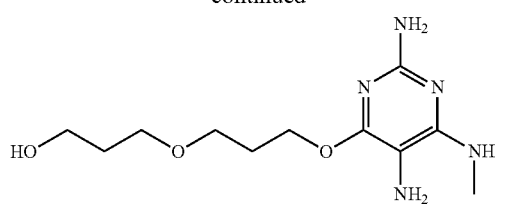

3-(3-{[2,5-diamino-6-methylamino)pyrimidin-4-yl]oxy}propoxy)propan-1-ol

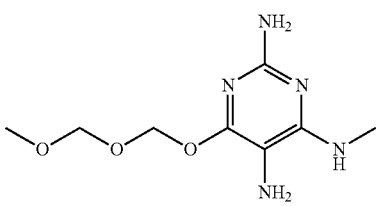

6-[(methoxymethoxy)methoxy]-N⁴-methylpyrimidine-2,4,5-triamine

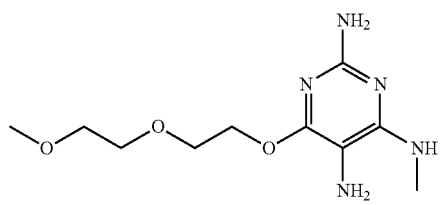

6-[2-(2-methoxyethoxy)ethoxy]-N⁴-methylpyrimidine-2,4,5-triamine

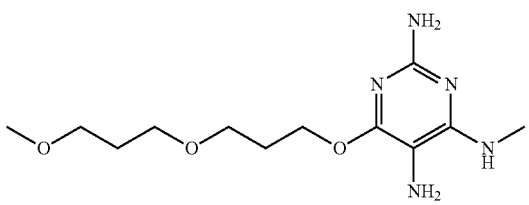

6-[3-(3-methoxypropoxy)propoxy]-N⁴-methylpyrimidine-2,4,5-triamine

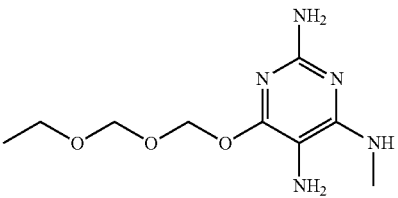

6-[(ethoxymethoxy)methoxy]-N⁴-methylpyrimidine-2,4,5-triamine

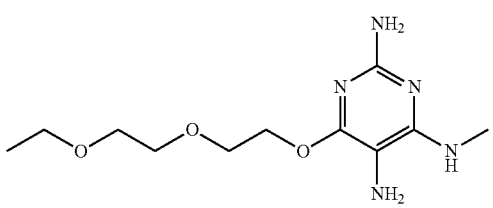

6-[2-(2-ethoxyethoxy)ethoxy]-N⁴-methylpyrimidine-2,4,5-triamine

-continued

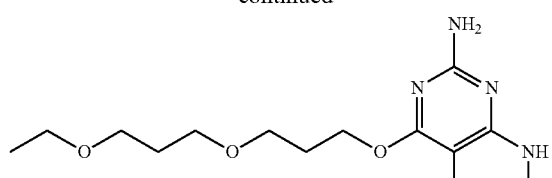

6-[3-(3-ethoxypropoxy)propoxy]-N$^4$-methylpyrimidine-2,4,5-triamine

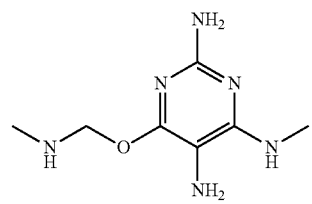

N$^4$-methyl-6-[(methylamino)methoxy]pyrimidine-2,4,5-triamine

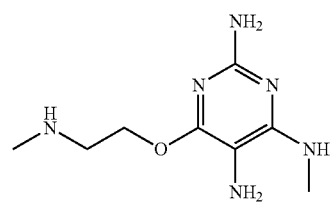

N$^4$-methyl-6-[2-(methylamino)ethoxy]pyrimidine-2,4,5-triamine

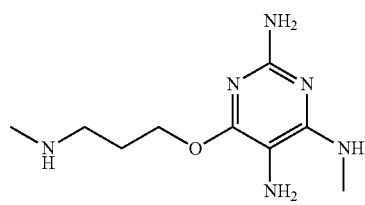

N$^4$-methyl-6-[3-(methylamino)propoxy]pyrimidine-2,4,5-triamine

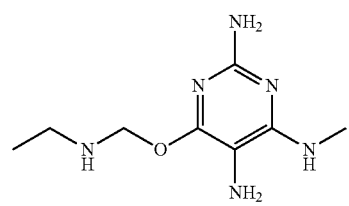

N$^4$-methyl-6-[(ethylamino)methoxy]pyrimidine-2,4,5-triamine

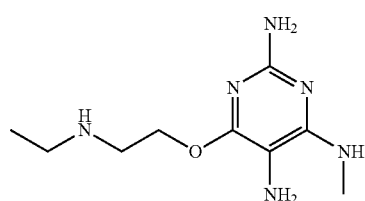

N$^4$-methyl-6-[2-(ethylamino)ethoxy]pyrimidine-2,4,5-triamine

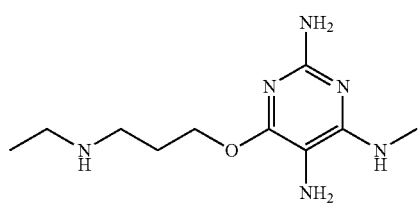

N$^4$-methyl-6-[2-(ethylamino)propoxy]pyrimidine-2,4,5-triamine

-continued

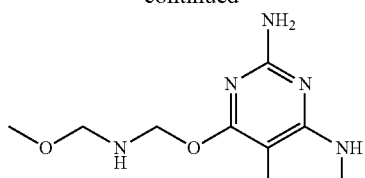

6-{[(methoxymethyl)amino]methoxy}pyrimidine-2,4,5-triamine

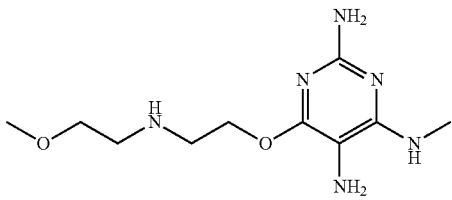

6-{2-[(2-methoxyethyl)amino]ethoxy}-N$^4$-methylpyrimidine-2,4,5-triamine

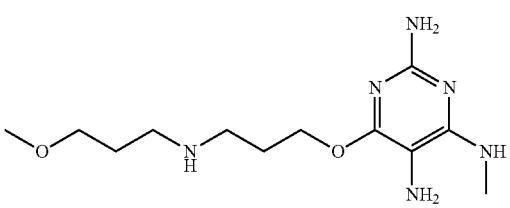

6-{[3-(methoxypropyl)amino]propoxy}-N$^4$-methylpyridine-2,4,5-triamine

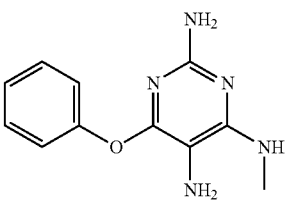

N$^4$-methyl-6-phenoxypyrimidine-2,4,5-triamine

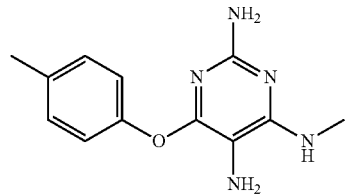

N$^4$-methyl-6-(4-methylphenoxy)pyrimidine-2,4,5-triamine

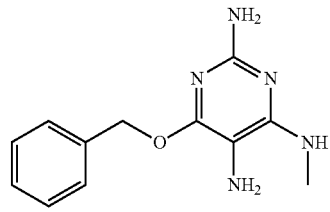

6-(benzyloxy)-N$^4$-methylpyrimidine-2,4,5-triamine

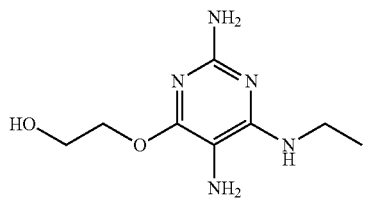

2-{[2,5-diamino-6-(ethylamino)pyrimidin-4-yl]oxy}ethanol

-continued

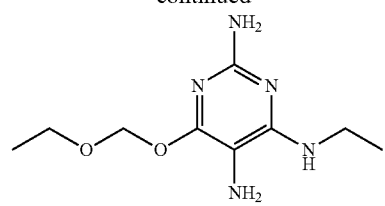

6-(ethoxymethoxy)-N$^4$-ethylpyrimidine-2,4,5-triamine

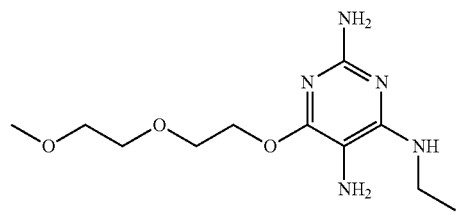

6-[2-(2-methoxyethoxy)ethoxy]-N$^4$-ethylpyrimidine-2,4,5-triamine

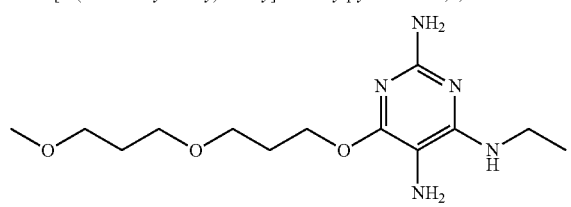

6-[3-(3-methoxypropoxy)propoxy]-N$^4$-ethylpyrimidine-2,4,5-triamine

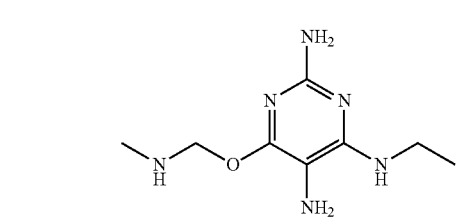

N$^4$-ethyl-6-[(methylamino)methoxy]pyrimidine-2,4,5-triamine

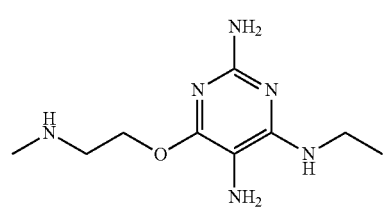

N$^4$-ethyl-6-[2-(methylamino)ethoxy]pyrimidine-2,4,5-triamine

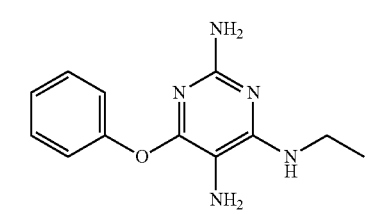

N$^4$-ethyl-6-phenoxypyrimidine-2,4,5-triamine

-continued

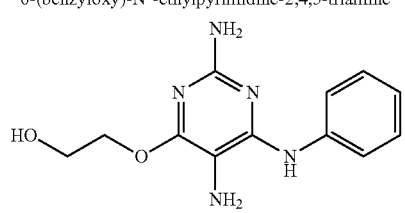

6-(benzyloxy)-N$^4$-ethylpyrimidine-2,4,5-triamine

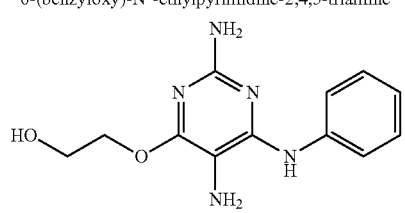

2-[(2,5-diamino-6-anilinopyrimidin-4-yl)oxy]ethanol

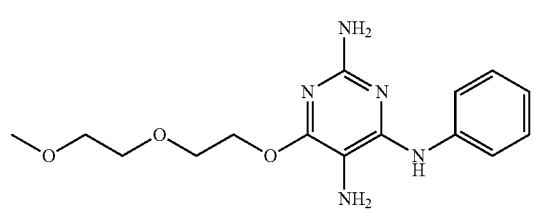

6-(ethoxymethoxy)-N$^4$-phenylpyrimidine-2,4,5-triamine

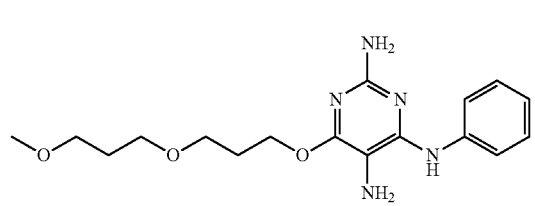

6-[2-(2-methoxyethoxy)ethoxy]-N$^4$-phenylpyrimidine-2,4,5-triamine

6-[3-(3-methoxypropoxy)propoxy]-N$^4$-phenylpyrimidine-2,4,5-triamine

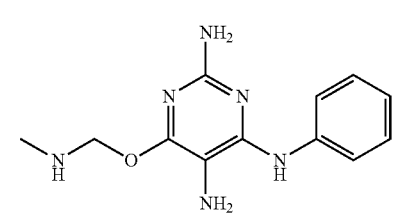

6-[(methylamino)methoxy]-N$^4$-phenylpyrimidine-2,4,5-triamine

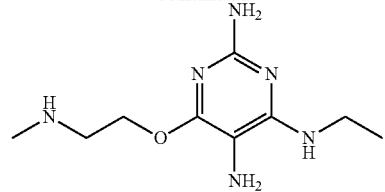

6-[2-(methylamino)ethoxy]-N⁴-phenylpyrimidine-2,4,5-triamine

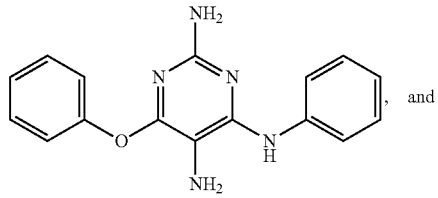

6-phenoxy-N⁴-phenylpyrimidine-2,4,5-triamine

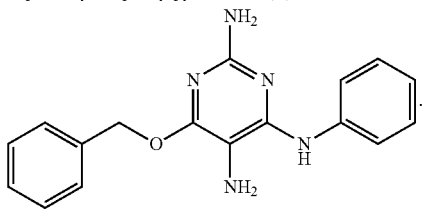

6-(benzyloxy)-N⁴-phenylpyrimidine-2,4,5-triamine

Agents preferred according to the invention are characterized in that they include the compounds according to formula (I) and/or the physiologically acceptable salts thereof in a proportion by weight of 0.001 to 5.0 wt %, preferably 0.025 to 2.5 wt %, especially preferably 0.05 to 2.0 wt %, and particularly preferably 0.1 to 1.5 wt %, with respect to the total weight of the agent ready for use.

The compounds of formula (I) can be included as unaccompanied color-changing compounds in the agent according to the invention. However, it is preferred according to the invention that the agent additionally includes at least one oxidation dye intermediate of the type of a coupler component.

Coupler components alone do not develop significant coloring in the oxidative dyeing process, but always require the presence of developer components.

Coupler components, within the meaning of the invention, permit at least one substitution of a chemical group of the coupler with the oxidized form of the developer component, wherein covalent bonds are formed between the coupler component and the developer component.

Coupler components according to the invention are preferably selected as at least one compound from one of the following classes:
m-aminophenol and/or the derivatives thereof,
m-diaminobenzene and/or the derivatives thereof,
o-diaminobenzene and/or the derivatives thereof,
o-aminophenol derivatives, such as o-aminophenol,
naphthalene derivatives having at least one hydroxy group,
di- or trihydroxybenzene and/or the derivatives thereof,
pyridine derivatives,
pyrimidine derivatives,
monohydroxyindole derivatives and/or monoaminoindole derivatives,
monohydroxyindoline derivatives and/or monoaminoindoline derivatives,
pyrazolone derivatives, such as 1-phenyl-3-methylpyrazol-5-one,
morpholine derivatives, such as 6-hydroxybenzomorpholine or 6-aminobenzomorpholine,
quinoxaline derivatives, such as 6-methyl-1,2,3,4-tetrahydroquinoxaline,
mixtures of two or more compounds from one or more of these classes are also in accordance with the invention in the context of this embodiment.

Coupler components especially preferred according to the invention are selected from among 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4,-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl) propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, 5-amino-4-chloro-o-cresol, 3-amino-6-methoxy-2-methylaminopyridine, 5-amino-4-chloro-o-cresol, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or the physiologically acceptable salts of the aforementioned compounds.

Particularly preferred coupler components are 1,3-bis-(2, 4-diaminophenoxy)propane, m-aminophenol, resorcinol, 5-amino-2-methylphenol, 2-methylresorcinol, 2-chloro-6-methyl-3-aminophenol, 2,7-dihydroxynaphthalene, 4-chlororesorcinol, 2,6-dihydroxy-3,4-dimethylpyridine, 1-amino-3-bis-(2-hydroxyethyl)aminobenzene (Lehmann's blue), 2,4-diaminophenoxyethanol, 5-amino-4-chloro-o-cresol, 3-amino-6-methoxy-2-methylaminopyridine, 5-amino-4-chloro-o-cresol, and/or a physiologically acceptable salt of these compounds.

The coupler components are used in the agents according to the invention preferably in an amount of 0.001 to 5.0 wt %, more preferably 0.025 to 2.5 wt %, especially preferably 0.05 to 2 wt %, and particularly 0.1 to 1.5 wt %, with respect to the total weight of the agent ready for use.

The following combinations of a developer according to the invention with selected couplers are especially advantageous:
2-[(2,5,6-triaminopyrimidin-4-yl)oxy]ethanol and one or more compounds selected from 5-amino-2-methylphenol, 1,3-bis(2,4-diaminophenoxy)propane, resorcinol, 2-methylresorcinol, 2-amino-3-hydroxypyridine, 3-amino-2-methylamino-6-methoxypyridine, and 2,7-dihydroxynaphthalene.
6-[2-(2-methoxyethoxy)ethoxy]pyrimidine-2,4,5-triamine and one or more compounds selected from 5-amino-2-methylphenol, 1,3-bis(2,4-diaminophenoxy)propane, resorcinol, 2-methylresorcinol, 2-amino-3-hydroxypyridine, 3-amino-2-methylamino-6-methoxypyridine, and 2,7-dihydroxynaphthalene.

According to the invention, in the combinations of oxidation dye intermediates preferred above, it can likewise be advantageous to use, instead of the uncharged compound, a physiologically acceptable salt of this compound.

In order to achieve balanced and subtle nuance development, it is advantageous according to the invention if further coloring components are included in the agent according to the invention.

Therefore, it can be preferred according to the invention that the agent includes at least one further coloring component that is selected from additional oxidation dye intermediates of the developer type and/or direct dyes.

In addition to the oxidation dye intermediates of the developer type according to formula (I), the agents according to the invention can additionally include at least one further developer component.

Preferred further developer components are selected from at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diamino-propan-2-ol, bis-(2-hydroxy-5-aminophenyl)methane, 1,3-bis-(2,5-diaminophenoxy)-propan-2-ol, N,N'-bis-(4-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine, and the physiologically acceptable salts of these compounds. Especially preferred additional developer components are p-toluylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and the physiologically acceptable salts thereof.

The additional developer components are preferably used in an amount of 0.0001 to 10 wt %, preferably 0.001 to 5 wt %, in each case with respect to the agent ready for use.

Furthermore, the agents according to the invention can include at least one direct dye. Direct dyes are dyes that attach directly to the hair and do not require an oxidative process to develop the color. Direct dyes are usually nitrophenylenediamines, nitroaminophenols, azo dyes, anthraquinones, or indophenols.

The direct dyes are used preferably in an amount of 0.001 to 20 wt %, particularly 0.05 to 5 wt %, in each case with respect to the entire application preparation. The total amount of direct dyes is preferably at most 3 wt %.

Direct dyes can be divided into anionic, cationic, and non-ionic direct dyes, which are selected and used by a person skilled in the art in accordance with the requirements of the carrier basis.

Preferred anionic direct dyes are the compounds known under the international designations or trademarks bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Preferred cationic direct dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), Basic Blue 99, Basic Brown 16 and Basic Brown 17, as well as Yellow 87, Basic Orange 31, and Basic Red 51.

Non-ionic nitro dyes and quinone dyes and neutral azo dyes in particular are suitable as non-ionic direct dyes. Preferred non-ionic direct dyes are the compounds known under the international designations or trademarks HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, and Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)-amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid, and 2-chloro-6-ethylamino-4-nitrophenol.

The agents according to the invention can also include dyes analogous to nature in addition to the compound according to formula (I). Compositions according to the invention that include precursors of dyes analogous to nature are preferably used as air-oxidative dye agents. Therefore, in this embodiment, said compositions are not mixed with an additional oxidant.

The dye precursors of dyes analogous to nature are used preferably in an amount of 0.001 to 5 wt % with respect to the entire application preparation. Derivatives of 5,6-dihydroxyindoline, particularly 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, and 5,6-dihydroxyindoline-2-carboxylic acid, and furthermore derivatives of 5,6-dihydroxyindole, particularly 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, and 5,6-dihydroxyindole-2-carboxylic acid, and physiologically acceptable salts of the aforementioned compounds, are especially well suited as precursors of hair dyes analogous to nature.

In the case of oxidative colorings, the development of the color can generally occur by means of atmospheric oxygen. However, a chemical oxidant is preferably used, especially if a lightening effect on human hair is desired in addition to the coloring. This lightening effect can be desired regardless of the dyeing method. Persulfates, peroxodisulfates, chlorites, hypochlorites, and particularly hydrogen peroxide and/or one of the solid addition products thereof to organic or inorganic compounds are possible as oxidants.

In order to prevent a premature, undesired reaction of the oxidation dye intermediates by means of the oxidant, the oxidation dye intermediates and the oxidant itself are expediently prepared separately from each other and not brought into contact until immediately before application.

Therefore, in a further embodiment of the present invention, agents are preferred which are characterized in that they are produced immediately before application by mixing at least two preparations, wherein the at least two preparations are provided in at least two separately prepared containers and wherein one container includes a dye agent (A), which includes at least one oxidation dye intermediate according to formula (I) in a cosmetic carrier, and a further container includes an oxidant preparation (B) including at least one oxidant.

The oxidant preparation (B) preferably includes hydrogen peroxide and/or one of the solid addition products thereof to organic or inorganic compounds, such as urea, melamine, and sodium borate, as an oxidant.

The amount of oxidant in the agent ready for use is preferably 0.5 to 12 wt %, preferably 2 to 10 wt %, particularly preferably 3 to 6 wt % (calculated as 100% $H_2O_2$), in each case with respect to the agent ready for use.

In a further preferred embodiment, the agent according to the invention is an agent for dyeing and possibly simultaneously lightening keratin fibers that includes hydrogen peroxide at preferably 0.5 to 15 wt %, more preferably 1 to 12.5 wt %, especially preferably 1.5 to 10 wt %, and particularly 2 to 6 wt %, in each case with respect to the total weight of the agent ready for use.

Such oxidant preparations are preferably aqueous, flowable oxidant preparations. Preferred preparations are characterized in that the flowable oxidant preparation includes, with respect to the weight thereof, water at 40 to 90 wt %, preferably 50 to 85 wt %, especially preferably 55 to 80 wt %, further preferably 60 to 77.5 wt %, and particularly 65 to 75 wt %.

However, according to the invention, the oxidation dye agent can also be applied to the hair together with a catalyst that activates the oxidation of the dye intermediates. Such catalysts are, for example, certain enzymes, iodides, quinones, or metal ions.

Furthermore, it has been proven to be advantageous if the oxidant preparations include at least one stabilizer or complexing agent. Common complexing agents and stabilizers preferred in the context of the present invention are, for example, polyoxycarboxylic acids, polyamines, ethylenediamine tetraacetic acid (EDTA), N-hydroxyethyl-ethylenediamine-triacetic acid, diethylenetriamine pentaacetic acid (DTPA), ethylenediamine disuccinic acid (EDDS), hydroxyethyliminodiacetic acid, nitridodiacetic acid-3-propionic acid, isoserine diacetic acid, N,N-di(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediamine diglutaric acid (EDGA), 2-hydroxypropylene diamine disuccinic acid (HPDS), glycinamide-N,N'-disuccinic acid (GADS), ethylenediamine-N,N'-diglutaric acid (EDDG), 2-hydroxypropylenediamine-N,N'-discuccinic acid (HPDDS), diaminoalkyldi(sulfosuccinic acid) (DDS), ethylenedicysteic acid (EDC), ethylenediamine-N,N'-bis(ortho-hydroxyphenyl)acetic acid (ED-DHA), N-2-hydroxyethylamine-N,N-diacetic acid, glyceryliminodiacetic acid, iminodiacetic acid-N-2-hydroxypropyl-sulfonic acid, aspartic acid-N-carboxymethyl-N-2,5-hydroxypropyl-3-sulfonic acid, β-alanine-N,N'-diacetic acid, aspartic acid-N,N'-diacetic acid, aspartic acid-N-monoacetic acid, dipicolinic acid, and the salts and/or derivatives thereof, geminal diphosphonic acids such as 1-hydroxyethane-1,1-diphosphonic acid (HEDP), the higher homologs thereof having up to 8 carbon atoms and derivatives thereof containing hydroxy or amino groups, and 1-aminoethane-1,1-diphosphonic acid, the higher homologs thereof having up to 8 carbon atoms and derivatives thereof containing hydroxy or amino groups, aminophosphonic acids such as ethylenediamine tetra(methylene phosphonic acid) (EDTMP), diethylenetriamine penta(methylene phosphonic acid) (DTPMP) and the higher homologs thereof, or nitrilotri(methylene phosphonic acid)), phosphono polycarboxylic acids such as 2-phosphonobutane-1,2,4-tricarboxylic acid, cyclodextrins, and alkali stannates (sodium stannate), alkali pyrophosphates (tetrasodium pyrophosphate, disodium pyrophosphate), alkali phosphates (sodium phosphate), and phosphoric acid and the salts thereof.

With the alkaline pH values of the treatment solutions, which pH values are required according to the invention, these complexing agents are at least partially present as anions. It is irrelevant whether they are introduced in the form of the acids or in the form of salts. If salts are used, alkali, ammonium, or alkylammonium salts, in particular sodium salts, are preferred.

Complexing agents preferred according to the invention are polycarboxylic acids containing nitrogen, particularly EDTA, and phosphonates, preferably hydroxyalkane phosphonates or aminoalkane phosphonates and particularly 1-hydroxyethane-1,1-diphosphonate (HEDP) or the di- or tetrasodium salt thereof and/or ethylenediaminetetramethylenephosphonate (EDTMP) and/or the hexasodium salt thereof and/or diethylenetriaminepentamethylenephosphonate (DTPMP) or the hepta- or octasodium salt thereof.

The dyeing preparation and optionally the oxidant preparation include further auxiliary substances and additives. It has proven preferable according to the invention if the dyeing preparation and/or the oxidant preparation includes at least one thickener. There are no restrictions in principle with regard to these thickeners. Both organic and purely inorganic thickeners can be used.

According to a first preferred embodiment, the thickener is an anionic, synthetic polymer. Preferred anionic groups are the carboxylate group and the sulfonate group.

Examples of anionic monomers of which the polymeric anionic thickeners can be composed are acrylic acid, methacrylic acid, crotonic acid, itaconic acid, maleic anhydride, and 2-acrylamido-2-methylpropane sulfonic acid. The acidic groups can be present completely or partially as sodium salt, potassium salt, ammonium salt, or mono- or triethanolammonium salt. Preferred monomers are maleic anhydride and particularly 2-acrylamido-2-methylpropane sulfonic acid and acrylic acid.

Preferred anionic homopolymers are un-cross-linked and cross-linked polyacrylic acids. Allyl ethers of pentaerythritol, of sucrose, and of propylene can be preferred cross-linking agents. Such compounds are commercially available, for example, under the trademark Carbopol®. Also preferred is the homopolymer of 2-acrylamido-2-methylpropane sulfonic acid, which is commercially available, for example, under the name Rheothik® 11-80.

In this first embodiment, it can also be preferable to use copolymers composed of at least one anionic monomer and at least one non-ionogenic monomer. With regard to the anionic monomers, reference is made to the substances listed above. Preferred non-ionogenic monomers are acrylamide, methacrylamide, acrylic acid esters, methacrylic acid esters, itaconic acid monoesters and diesters, vinylpyrrolidinone, vinyl ethers, and vinyl esters.

The anionic acrylic acid and/or methacrylic acid polymers or copolymers are included in the agents according to the invention preferably in an amount of 0.1 to 10 wt %, especially preferably 1 to 5 wt %, in each case with respect to the weight of the agent.

Preferred anionic copolymers are, for example, copolymers of acrylic acid, methacrylic acid, or the $C_1$-$C_6$ alkyl esters thereof, which are sold under the INCI declaration Acrylates Copolymers. A preferred commercial product is, for example, Aculyn® 33 from Rohm & Haas. Copolymers of acrylic acid, methacrylic acid, or the $C_1$-$C_6$ alkyl esters thereof and of the esters of an ethylenically unsaturated acid and an alkoxylated fatty alcohol are also preferred. Suitable ethylenically unsaturated acids are, in particular, acrylic acid, methacrylic acid, and itaconic acid; suitable alkoxylated fatty alcohols are, in particular, Steareth-20 or Ceteth-20. Such copolymers are sold by Rohm & Haas under the trademark Aculyn® 22 and by National Starch under the trademarks Structure® 2001 and Structure® 3001.

Preferred anionic copolymers are also acrylic acid/acrylamide copolymers and, particularly, polyacrylamide copolymers having monomers that contain sulfonic acid groups. An especially preferred anionic copolymer is composed of 70 to 55 mol % acrylamide and 30 to 45 mol % 2-acrylamido-2-methylpropane sulfonic acid, wherein the sulfonic acid group is completely or partially present as sodium salt, potassium salt, ammonium salt, or mono- or triethanolammonium salt. This copolymer can also be present in a cross-linked state, wherein preferably polyolefinically unsaturated compounds such as tetraallyloxythan, allyl sucrose, allyl pentaerythritol, and methylenebisacrylamide are used as cross-linking agents. Such a polymer is contained in the commercial products Sepigel® 305 and Simulgel® 600 from SEPPIC. The use of these compounds, which include a hydrocarbon mixture ($C_{13}$-$C_{14}$ isoparaffin or isohexadecane) and a non-ionogenic emulsifier (Laureth-7 or Polysorbate-80) in addition to the polymer component, has proven to be especially advantageous in the context of the teaching according to the invention.

Polymers of maleic anhydride and methyl vinyl ether, in particular such having cross-links, are also preferred thickeners. A maleic acid/methyl vinyl ether copolymer cross-linked by means of 1,9-decadiene is commercially available under the name Stabileze® QM.

The agent according to the invention preferably can additionally include at least one anionic acrylic acid and/or methacrylic acid polymer or copolymer. Preferred polymers of this type are:
  Polymers, e.g., composed of at least 10 wt % of acrylic acid low-alkyl ester, 25 to 70 wt % of methacrylic acid, and optionally up to 40 wt % of a further comonomer.
  Mixed polymers composed of 50 to 75 wt % of ethyl acrylate, 25 to 35 wt % of acrylic acid, and 0 to 25 wt % of other comonomers known. Suitable dispersions of this type are commercially available, for example under the trademark Latekoll® D (BASF).
  Copolymers composed of 50 to 60 wt % of ethyl acrylate, 30 to 40 wt % of methacrylic acid, and 5 to 15 wt % of acrylic acid, cross-linked by means of ethylene glycol dimethacrylate.

According to a further embodiment, the thickener is a cationic synthetic polymer. Preferred cationic groups are quaternary ammonium groups. In particular, such polymers in which the quaternary ammonium group is bonded by means of a $C_1$-$C_4$ hydrocarbon group to a polymer main chain constructed of acrylic acid, methacrylic acid, or the derivatives thereof have proven to be especially suitable.

Homopolymers of general formula (HP-1),

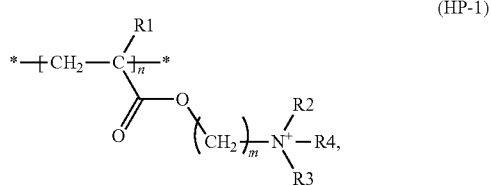

(HP-1)

in which R1=—H or —$CH_3$, R2, R3, and R4 are selected, independently of each other, from $C_1$-$C_4$ alkyl, alkenyl, or hydroxyalkyl groups, m=1, 2, 3, or 4, n is a natural number, and $X^-$ is a physiologically acceptable organic or inorganic anion, and copolymers composed substantially of the monomer units stated in formula (HP-1) and non-ionogenic monomer units, are especially preferred cationic polymeric gelling agents. With regard to these polymers, those to which at least one of the following conditions applies are preferred according to the invention:
  R1 stands for a methyl group,
  R2, R3, and R4 stand for methyl groups,
  m has the value 2.

Halogenide ions, sulfate ions, phosphate ions, methosulfate ions, and organic ions such as lactate, citrate, tartrate, and acetate ions, for example, are considered as physiologically acceptable counterions $X^-$. Halogenide ions, particularly choride, are preferred.

An especially suitable homopolymer is the cross-linked, if desired, poly(methacryloxyethyltrimethylammonium chloride) having the INCI designation Polyquaternium-37. The cross-linking, if desired, can be performed by means of olefinically polyunsaturated compounds, such as divinylbenzene, tetraallyloxyethane, methylenebisacrylamide, diallyl ether, polyallylpolyglycerylether, or allyl ethers of sugars or sugar derivatives such as erythritol, pentaerythritol, arabitol, mannitol, sorbitol, sucrose, or glucose. Methylenebisacrylamide is a preferred cross-linking agent.

The homopolymer is preferably used in the form of a non-aqueous polymer dispersion, which should have a polymer fraction of at least 30 wt %. Such polymer dispersions are commercially available under the names Salcare® SC 95 (approx. 50% polymer fraction, further component: mineral oil (INCI designation: Mineral Oil) and tridecyl-polyoxypropylene-polyoxyethylene-ether (INCI designation: PPG-1-Trideceth-6)) and Salcare® SC 96 (approx. 50% polymer fraction, further components: mixture of diesters of propylene glycol with a mixture of caprylic and capric acid (INCI designation: Propylene Glycol Dicaprylate/Dicaprate) and tridecyl-polyoxypropylene-polyoxyethylene-ether (INCI designation: PPG-1-Trideceth-6)).

Copolymers having monomer units according to formula (HP-1) include preferably acrylamide, methacrylamide, acrylic acid $C_1$-$C_4$ alkyl ester, and methacrylic acid $C_1$-$C_4$ alkyl ester as non-ionogenic monomer units. Among these non-ionogenic monomers, acrylamide is especially preferred. These copolymers also can be cross-linked as in the case of the homopolymers described above. A copolymer preferred according to the invention is the cross-linked acrylamide methacroyloxyethyl trimethylammonium chloride copolymer. Such copolymers in which the monomers are present in a weight ratio of approximately 20:80 are commercially available as an approx. 50% non-aqueous polymer dispersion under the name Salcare® SC 92.

In a further preferred embodiment, naturally occurring thickeners are used. Preferred thickeners of this embodiment are, for example, non-ionic guar gums. According to the invention, both modified and unmodified guar gums can be used. Unmodified guar gums are sold, for example, under the trademark Jaguar® C by Rhone Poulenc. Modified guar gums preferred according to the invention include $C_1$-$C_6$ hydroxyalkyl groups. The groups hydroxymethyl, hydroxyethyl, hydroxypropyl, and hydroxybutyl are preferred. Guar gums modified in such a way are known in the prior art and can be produced, for example, by reacting the guar gums with alkylene oxides. The degree of hydroxyalkylation, which corresponds to the number of consumed alkylene oxide molecules in relationship to the number of free hydroxy groups of the guar gums, is preferably between 0.4 and 1.2. Guar gums modified in such a way are commercially available under the trademarks Jaguar® HP8, Jaguar® HP60, Jaguar® HP120, Jaguar® DC 293, and Jaguar® HP105 from Rhone Poulenc.

Further suitable natural thickeners are likewise already known from the prior art.

Also preferred according to this embodiment are biosaccharide gums of microbial origin, such as the scleroglucan gums or xanthan gums, gums from plant exudates, such as gum arabic, ghatti gum, karaya gum, tragacanth gum, carrageenan gum, agar-agar, locust bean gum, pectins, alginates, starch fractions and derivatives such as amylose, amylopectin, and dextrins, and cellulose derivatives such as methyl cellulose, carboxyalkyl celluloses, and hydroxyalkyl celluloses.

Preferred hydroxyalkyl celluloses are, in particular, the hydroxyethyl celluloses which are sold under the names Cellosize® from Amerchol and Natrosol® from Hercules. Suitable carboxyalkyl celluloses are, in particular, the carboxymethyl celluloses which are sold under the names Blanose® from Aqualon, Aquasorb® and Ambergum® from Hercules, and Cellgon® from Montello.

Also preferred are starch and the derivatives thereof. Starch is a storage substance of plants that occurs especially in tubers and roots, in grain seeds, and in fruits and can be obtained from a large number of plants in high yields. The polysaccharide, which is insoluble in cold water and forms a colloidal solution in boiling water, can be obtained from, for example, potatoes, cassava, sweet potatoes, maranta, corn, grains, rice, pulses such as peas and beans, bananas, or the pith of certain palm types (for example, the sago palm). Natural starches obtained from plants and/or chemically or physically modified starches can be used according to the invention. A modification can be achieved, for example, by introducing different functional groups at one or more of the hydroxyl groups of the starch. Typical modifications are esters, ethers, or amides of the starch having optionally substituted $C_1$-$C_{40}$ groups. Especially advantageous is a corn starch etherified by means of a 2-hydroxypropyl group, which is sold, for example, by National Starch under the trademark Amaze®.

Non-ionic, fully synthetic polymers, such as polyvinyl alcohol or polyvinylpyrrolidone, can also be used as thickeners according to the invention. Preferred non-ionic, fully synthetic polymers are sold, for example, by BASF under the trademark Luviskol®. Such non-ionic polymers also enable, in addition to their excellent thickening properties, a clear improvement of the sensory feel of the resulting preparations.

Phyllosilicates (polymeric, crystalline sodium disilicates) have proven especially suitable as inorganic thickeners according to the present invention. In particular, clays, particularly magnesium aluminum silicates, such as bentonite, especially smectites, such as montmorillonite or hectorite, which optionally also can be suitably modified, and synthetic phyllosilicates, such as the magnesium phyllosilicate sold by Süd Chemie under the trademark Optigel®, are preferred.

In order to further increase the performance of the oxidant preparation, additionally at least one optionally hydrated $SiO_2$ compound can be added to the composition according to the invention. It can be preferred according to the invention to use the optionally hydrated $SiO_2$ compounds in amounts of 0.05 wt % to 15 wt %, especially preferably in amounts of 0.15 wt % to 10 wt %, and exceptionally preferably in amounts of 0.2 wt % to 5 wt %, in each case with respect to the water-free composition according to the invention. The amount specifications represent the content of the $SiO_2$ compounds (without the water fraction thereof) in the agents.

With regard to the optionally hydrated $SiO_2$ compounds, the present invention is, in principle, not subject to any restrictions. Silicic acids, the oligomers and polymers thereof and the salts thereof are preferred. Preferred salts are the alkali salts, in particular the potassium and sodium salts. The sodium salts are exceptionally preferred.

The optionally hydrated $SiO_2$ compounds can be present in various forms. According to the invention, the $SiO_2$ compounds are preferably used in the form of silica gels or especially preferably as water glass. Some of these $SiO_2$ compounds can be present in an aqueous solution.

Exceptionally preferred according to the invention are water glasses which are formed from a silicate of the formula $(SiO_2)_n(Na_2O)_m(K_2O)_p$, wherein n stands for a positive rational number and m and p stand, independently of each other, for a positive rational number or for 0, with the proviso that at least one of the parameters m or p is different from 0 and the ratio between n and the sum of m and p lies between 1:4 and 4:1. Metasilicates in which the ratio between n and the sum of m and p is 1:2 or less are preferred.

In addition to the components described by the empirical formula, the water glasses can also include further additives, such as phosphates or magnesium salts, in small amounts.

Water glasses especially preferred according to the invention are sold by, among others, Henkel under the names Ferrosil® 119, Natronwasserglas 40/42, Portil® A, Portil® AW, and Portil® W and by Akzo under the name Britesil® C20.

The preparation (A) and/or optionally the oxidant preparation (B) are preferably prepared as flowable preparations.

An emulsifier or a surfactant is also preferably added to the flowable preparations (A) and/or (B), wherein surface-active substances are designated as surfactants or as emulsifiers depending on the field of application and are selected from anionic, cationic, zwitterionic, amphoteric, and nonionic surfactants and emulsifiers. These substances are described in detail below.

All anionic surface-active substances suitable for use on the human body are suitable as anionic surfactants in preparations according to the invention. These substances are characterized by an anionic group, such as a carboxylate, sulfate, sulfonate, or phosphate group, that makes the substance water-soluble, and by a lipophilic alkyl group having approximately 8 to 30 C atoms. Additionally, glycol or polyglycol ether groups, ester, ether, and amide groups, and hydroxyl groups can be contained in the molecule. Examples of suitable anionic surfactants are, in each case in the form of the sodium, potassium, and ammonium salts and the mono-, di-, and trialkanol ammonium salts having 2 to 4 C atoms in the alkanol group, linear and branched fatty acids having 8 to 30 C atoms (soaps), ether carboxylic acids of the formula $RO(CH_2CH_2O)_xCH_2COOH$, in which R is a linear alkyl group having 8 to 30 C atoms and x=0 or 1 to 16, acyl sarcosides having 8 to 24 C atoms in the acyl group, acyl taurides having 8 to 24 C atoms in the acyl group, acyl isethionates having 8 to 24 C atoms in the acyl group, sulfosuccinic acid mono- and dialkyl esters having 8 to 24 C atoms in the alkyl group and sulfosuccinic acid monoalkyl polyoxyethyl esters having 8 to 24 C atoms in the alkyl group and 1 to 6 oxyethyl groups, linear alkane sulfonates having 8 to 24 C atoms, linear α-olefin sulfonates having 8 to 24 C atoms, sulfonates of unsaturated fatty acids having 8 to 24 C atoms and 1 to 6 double bonds, α-sulfo fatty acid methyl esters of fatty acids having 8 to 30 C atoms,
alkyl sulfates and alkyl ether sulfates of the formula RO(CH$_2$CH$_2$O)$_x$SO$_3$H, in which R is a preferably linear alkyl group having 8 to 30 C atoms and x=0 or 1 to 12,
mixtures of surface-active hydroxysulfonates,
sulfated hydroxyalkl polyethylene glycol ethers and/or hydroxyalkylene propylene glycol ethers,
esters of tartaric acid and citric acid with alcohols that are addition products of approximately 2-15 molecules of ethylene oxide and/or propylene oxide to fatty alcohols having 8 to 22 C atoms,
alkyl and/or alkenyl ether phosphates of the formula

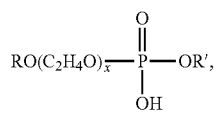

in which R preferably stands for an aliphatic, optionally unsaturated hydrocarbon group having 8 to 30 carbon atoms, R' stands for hydrogen, a group (CH$_2$CH$_2$O)$_y$R, and x and y stand, independently of each other, for a number from 1 to 10,
sulfated fatty acid alkylene glycol esters of the formula RC(O)O(alkO)$_n$SO$_3$H, in which R stands for a linear or branched, aliphatic, saturated and/or unsaturated alkyl group having 6 to 22 C atoms, alk stands for CH$_2$CH$_2$, CHCH$_3$CH$_2$, and/or CH$_2$CHCH$_3$, and n stands for a number from 0.5 to 5,
monoglyceride sulfates and monoglyceride ether sulfates.

Preferred anionic surfactants are alkyl sulfates, alkyl ether sulfates, and ether carboxylic acids having 10 to 18 C atoms in the alkyl group and up to 12 glycol ether groups in the molecule.

Those surface-active compounds that bear at least one quaternary ammonium group and at least one carboxylate, sulfonate, or sulfate group in the molecule are referred to as zwitterionic surfactants. Especially suitable zwitterionic surfactants are the so-called betaines such as the N-alkyl-N,N-dimethyl ammonium glycinates, for example coco alkyl dimethyl ammonium glycinate, N-acyl-aminopropyl-N,N-dimethyl ammonium glycinates, for example coco acyl aminopropyl dimethyl ammonium glycinate, and 2-alkyl-3-carboxymethyl-3-hydroxyethylimidazolines having 8 to 18 C atoms each in the alkyl or acyl group, and coco acyl aminoethyl hydroxyethyl carboxymethyl glycinate. A preferred zwitterionic surfactant is the fatty acid amide derivative known under the INCI designation Cocamidopropyl Betaine.

Those surface-active compounds that include at least one free amino group and at least one —COOH— or —SO$_3$H group in addition to a C$_8$-C$_{24}$ alkyl or acyl group in the molecule and are capable of forming inner salts are referred to as amphoteric surfactants. Examples of suitable amphoteric surfactants are N-alkyl glycines, N-alkyl propionic acids, N-alkyl aminobutyric acids, N-alkyl imino dipropionic acids, N-hydroxyethyl-N-alkyl amidopropyl glycines, N-alkyl taurines, N-alkyl sarcosines, 2-alkyl aminopropionic acids, and alkyl aminoacetic acids each having approximately 8 to 24 C atoms in the alkyl group. Especially preferred amphoteric surfactants are N-coco alkyl aminopropionate, coco acyl aminoethyl aminopropionate, and C$_{12}$-C$_{18}$ acyl sarcosine.

Furthermore, it has proven advantageous if the dye agents and lightening agents according to the invention include further, non-ionogenic interface-active substances. Non-ionic surfactants include, for example, a polyol group, a polyalkylene glycol ether group, or a combination of polyol group and polyglycol ether group as a hydrophilic group. Such compounds are, for example,
addition products of 1 to 50 mol of ethylene oxide and/or 0 to 5 mol of propylene oxide to linear and branched fatty alcohols having 8 to 30 C atoms, such as lauryl, myristyl, cetyl, but also stearyl, isostearyl, and oleyl alcohol, to fatty acids having 8 to 30 C atoms and to alkylphenols having 8 to 15 C atoms in the alkyl group,
addition products, which are terminal group-closed by means of a methyl or C$_2$-C$_6$ alkyl group, of 1 to 50 mol of ethylene oxide and/or 0 to 5 mol of propylene oxide to linear and branched fatty alcohols having 8 to 30 C atoms, to fatty acids having 8 to 30 C atoms, and to alkylphenols having 8 to 15 C atoms in the alkyl group, such as the types available under the sales names Dehydol® LS and Dehydol® LT (Cognis),
polyglycerol esters and alkoxylated polyglycerol esters, such as poly(3)glycerol diisostearate (commercial product: Lameform® TGI (Henkel)) and poly(2)glycerol polyhydroxystearate (commercial product: Dehymuls® PGPH (Henkel)),
polyol fatty acid esters, such as the commercial product Hydagen® HSP (Cognis) or Sovermol types (Cognis),
more highly alkoxylated, preferably propoxylated and particularly ethoxylated, mono-, di-, and triglycerides, such as glycerol monolaurate+20 ethylene oxide and glycerol monostearate+20 ethylene oxide,
amine oxides,
hydroxy mixed ethers,
sorbitan fatty acid esters and addition products of ethylene oxide to sorbitan fatty acid esters such as the polysorbates and sorbitan monolaurate+20 mol of ethylene oxide (EO),
sugar fatty acid esters and addition products of ethylene oxide to sugar fatty acid esters,
addition products of ethylene oxide to fatty acid alkanolamides and fatty amines,
fatty acid-N-alkylglucamides,
alkylphenols and alkylphenol alkoxylates having 6 to 21, particularly 6 to 15, carbon atoms in the alkyl chain and 1 to 30 ethylene oxide and/or propylene oxide units. Preferred representatives of this class are, for example, nonylphenol+9 EO and octylphenol+8 EO;
alkyl polyglycosides according to the general formula RO—(Z)$_x$, wherein R stands for alkyl, Z stands for sugar, and x stands for the number of sugar units. The alkyl polyglycosides that are usable according to the invention can include only one certain alkyl group R. However, these compounds are typically produced from natural fats and oils or mineral oils. In this case, mixtures are present as alkyl groups R in accordance with the starting compounds or in accordance with the particular processing of these compounds. The alkoxylated homologs of said alkyl polyglycosides can also be used according to the invention. These homologs can include, on average, up to 10 ethylene oxide and/or propylene oxide units per alkyl glycoside unit.

The anionic, non-ionic, zwitterionic, or amphoteric surfactants are used in amounts of 0.1 to 45 wt %, preferably 1 to 30 wt %, and exceptionally preferably 1 to 15 wt %, with respect to the total amount of the agent ready for use.

Cationic surfactants of the type of the quaternary ammonium compounds, the esterquats, and the amidoamines are also preferred according to the invention. Preferred quaternary ammonium compounds are ammonium halogenides, particularly chlorides and bromides, such as alkyltrimethylammonium chlorides, dialkyldimethylammonium chlorides, and trialkylmethylammonium chlorides, for example, cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride, and the imidazolium compounds known under the INCI designations Quaternium-27 and Quaternium-83. The long alkyl chains of the aforementioned surfactants have preferably 10 to 18 carbon atoms. Further cationic surfactants that are usable according to the invention are the quaternized protein hydrolysates.

The alkylamidoamines are usually produced by amidating natural or synthetic fatty acids and fatty acid fractions with dialkylaminoamines and are distinguished especially by their good biodegradability in addition to a good conditioning effect. A compound from this substance group that is particularly suitable according to the invention is stearamidopropyl dimethylamine, which is commercially available under the name Tegoamid® S 18.

Quaternary ester compounds, so-called "esterquats," are also very well biodegradable. Esterquats are known substances that include both at least one ester function and at least one quaternary ammonium group as a structural element. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are sold, for example, under the trademarks Stepantex®, Dehyquart®, and Armocare®. The products Armocare® VGH-70, an N,N-bis(2-palmitoyloxyethyl)dimethylammonium chloride, and Dehyquart® F-75, Dehyquart® C-4046, Dehyquart® L80, and Dehyquart® AU-35 are examples of such esterquats.

The cationic surfactants are included in the agents used according to the invention preferably in amounts of 0.05 to 10 wt % with respect to the entire agent. Amounts of 0.1 to 5 wt % are especially preferred.

In a preferred embodiment, non-ionic, zwitterionic, and/or amphoteric surfactants and the mixtures thereof can be preferred.

In a further preferred embodiment, the effect of the active ingredient according to the invention can be increased by means of emulsifiers. Such emulsifiers are, for example,

- addition products of 4 to 30 mol of ethylene oxide and/or 0 to 5 mol of propylene oxide to linear fatty alcohols having 8 to 22 C atoms, to fatty acids having 12 to 22 C atoms, and to alkylphenols having 8 to 15 C atoms in the alkyl group,
- $C_{12}$-$C_{22}$ fatty acid mono- and diesters of addition products of 1 to 30 mol of ethylene oxide to polyols having 3 to 6 carbon atoms, particularly to glycerol,
- addition products of ethylene oxide and polyglycerol to methylglucoside fatty acid esters, fatty acid alkanolamides, and fatty acid glucamides,
- $C_8$-$C_{22}$ alkylmono- and -oligoglycosides and the ethoxylated analogs thereof, wherein degrees of oligomerization of 1.1 to 5, particularly 1.2 to 2.0, and glucose as a sugar component are preferred,
- mixtures of alkyl (oligo-)glucosides and fatty alcohols, such as the commercially available product Montanov® 68,
- addition products of 5 to 60 mol of ethylene oxide to castor oil and hardened castor oil,
- partial esters of polyols having 3 to 6 carbon atoms with saturated fatty acids having 8 to 22 C atoms,
- sterols, wherein sterols are understood to mean a group of steroids that bear a hydroxyl group at C atom 3 of the steroid skeleton and are isolated both from animal tissue (zoosterols) and from plant fats (phytosterols). Examples of zoosterols are cholesterol and lanosterol. Examples of suitable phytosterols are ergosterol, stigmasterol, and sitosterol. Sterols are also isolated from fungi and yeasts (the so-called mycosterols),
- phospholipids, especially glucose phospholipids, which are obtained, for example as lecithins or phosphatidylcholines, for example from egg yolk or plant seeds (e.g., soybeans),
- fatty acid esters of sugars and sugar alcohols, such as sorbitol,
- polyglycerols and polyglycerol derivatives such as polyglycerol poly-12-hydroxystearate (commercial product Dehymuls® PGPH),
- linear and branched fatty acids having 8 to 30 C atoms and the Na, K, ammonium, Ca, Mg, and Zn salts thereof.

The agents according to the invention include the emulsifiers preferably in amounts of 0.1 to 25 wt %, particularly 0.5 to 15 wt %, with respect to the total amount of the agent ready for use.

Non-ionogenic emulsifiers or surfactants having an HLB of 10-15 can be especially preferred according to the invention. Among the emulsifier types mentioned, the emulsifiers that do not include any ethylene oxide and/or propylene oxide in the molecule can be exceptionally preferred.

Furthermore, the agents according to the invention can include further active ingredients, auxiliary substances, and additives, such as

- non-ionic polymers, such as vinylpyrrolidinone/vinyl acrylate copolymers, polyvinylpyrrolidinone, vinylpyrrolidinone/vinyl acetate copolymers, polyethylene glycols, and polysiloxanes;
- silicones, such as volatile or non-volatile, straight-chain, branched, or cyclic, cross-linked or un-cross-linked polyalkylsiloxanes (such as dimethicones or cyclomethicones), polyarylsiloxanes and/or polyalkylarylsiloxanes, particularly polysiloxanes having organofunctional groups, such as substituted or unsubstituted amines (amodimethicones), carboxyl, alkoxy, and/or hydroxyl groups (dimethicone copolyols), linear polysiloxane(A)-polyoxyalkylene(B) block copolymers, grafted silicone polymers having an organic backbone that does not include silicone or having a polysiloxane backbone, such as the commercial product Abil B 8832 from Degussa sold under the INCI designation Bis-PEG/PPG-20/20 Dimethicone, or the mixtures thereof;
- cationic polymers such as quaternized cellulose ethers, polysiloxanes having quaternary groups, dimethyldiallylammonium chloride polymers, acrylamide/dimethyldiallylammonium chloride copolymers, dimethylaminoethyl methyacrylate/vinylpyrrolidinone copolymers quaternized with diethyl sulfate, vinylpyrrolidinone/imidazolinium methochloride copolymers, and quaternized polyvinyl alcohol;
- zwitterionic and amphoteric polymers, such as acrylamidopropyltrimethylammonium chloride/acrylate copolymers and octylacrylamide/methyl methacrylate/tert-butylamino ethyl methacrylate/2-hydroxypropyl methacrylate copolymers, diallyldimethylammonium chloride/acrylate copolymers, t-butylaminoethyl methacrylate/N-(1,1,3,3-tetramethylbutyl)acrylamide/acrylate(/methacrylate) copolymers,
- anionic polymers, such as polyacrylic acids, cross-linked polyacrylic acids, vinyl acetate/crotonic acid copolymers, vinylpyrrolidinone/vinyl acrylate copolymers, vinyl acetate/butyl maleate/isobornyl acrylate copolymers, methyl vinyl ether/maleic anhydride copolymers, and acrylic acid/ethyl acrylate/N-t-butylacrylamide terpolymers, further thickeners, such as agar-agar, guar gum, alginates, xanthan gum, gum arabic, karaya gum, locust bean gum, linseed gums, dextranes, cellulose derivatives, e.g., methyl cellulose, hydroxyalkyl cellulose, and carboxymethyl cellulose, starch fractions and derivatives such as amylose, amylopectin, and dextrins, clays, such as bentonite, or fully synthetic hydrocolloids, such as polyvinyl alcohol, structurants, such as glucose, maleic acid, and lactic acid, hair-conditioning compounds, such as phospholipids, for example soy lecithin, egg lecithin, and cephalins, and silicone oils, perfume oils, dimethyl isosorbide, and cyclodextrins, solvents and solubilizers, such as ethanol, isopropanol, ethylene glycol, propylene glycol, glycerol, and diethylene glycol, fiber-structure-improving active ingredients, particularly mono-, di-, and oligosaccharides, such as glucose, galactose, fructose, fruit sugar, and lactose, quaternized amines, such as methyl-1-alkylamidoethyl-2-alkylimidazolinium-methosulfate, defoamers, such as silicones, dyes for coloring the agent, anti-dandruff active ingredients, such as piroctone olamine, zinc omadine, and climbazole, amino acids and oligopeptides, particularly arginine and/or serine, animal- and/or plant-based protein hydrolysates, such as elastin, collagen, keratin, silk, and milk-protein protein hydrolysates, or almond, rice, pea, potato, and wheat protein hydrolysates, and in the form of the fatty acid condensations products thereof or optionally anionically or cationically modified derivatives thereof, plant oils, such as macadamia nut oil, kukui nut oil, palm oil, amaranth seed oil, peach kernel oil, avocado oil, olive oil, coconut oil, rapeseed oil, sesame oil, jojoba oil, soybean oil, peanut oil, evening primrose oil, and tea-tree oil, light stabilizers, particularly derivatized benzophenones, cinnamic acid derivatives, and triazines, substances for adjusting the pH value, such as common acids, in particular edible acids and bases, active ingredients, such as panthenol, pantothenic acid, pantolactone, allantoin, pyrrolidinone carboxylic acids and the salts thereof, and bisabolol, polyphenols, particularly hydroxycinnamic acids, 6,7-dihydroxycoumarins, hydroxybenzoic acids, catechins, tannins, leucoanthocyanidins, anthocyanidins, flavanones, flavones, and flavonols;

ceramides, preferably the sphingolipids, such as ceramide I, ceramide II, ceramide 1, ceramide 2, ceramide 3, ceramide 5, and ceramide 6, or pseudo-ceramides, such as in particular N—($C_8$-$C_{22}$-acyl)-($C_8$-$C_{22}$-acyl)-hydroxyproline, vitamins, provitamins, and vitamin precursors, particularly such of the groups A, $B_3$, $B_5$, $B_6$, C, E, F, and H, plant extracts, such as the extracts from aloe vera, angelica, anise, apricot, benzoin, bergamot, birch, stinging nettle, calamus, cassis, costus, marshmallow, oak bark, elemi, tarragon, spruce needle, galbanum, geranium, ginseng, grapefruit, guaiacum, green tea, witch hazel, restharrow, hop, coltsfoot, ginger root, iris, jasmine, camomile, cardamom, clover, burdock root, pine, kiwi, coconut, coriander, caraway, mountain pines, lavender, lemongrass, lily, lime, lime blossoms, litchi, mace, mallow, almond, mango, balm, melon, meristem, myrrh, neroli, olibanum, opoponax, orange, patchouli, petitgrain, stone pine, wild thyme, rooibos, roses, rosemary, horse chestnut, sandalwood, sage, horsetail, yarrow, celery, fir, garden thyme, juniper, vine leaves, whitethorn, wheat, lady's smock, ylang-ylang, cedar, and lemon, cholesterol, consistency-providing agents, such as sugar esters, polyol esters, or polyol alkyl ethers, fats and waxes, such as spermaceti wax, beeswax, montan wax, and paraffins, fatty acid alkanolamides, swelling and penetrating agents, such as glycerol, propylene glycol monoethyl ethers, carbonates, hydrogen carbonates, guanidines, ureas, and primary, secondary, and tertiary phosphates, opacifiers, such as latex, styrene/PVP and styrene/acrylamide copolymers, pearlizing agents, such as ethylene glycol mono- and distearate, and PEG-3 distearate, pigments, stabilizers for hydrogen peroxide and other oxidants, propellants, such as propane/butane mixtures, $N_2O$, dimethyl ether, $CO_2$, and air, antioxidants.

A person skilled in the art will make the selection of these further substances in accordance with the desired properties of the agents.

With regard to further optional components and the amounts of these components that are used, reference is made explicitly to the pertinent handbooks known to a person skilled in the art, such as Kh. Schrader, "Grundlagen and Rezepturen der Kosmetika", $2^{nd}$ edition, Hüthig Buch Verlag, Heidelberg, 1989.

The additional active ingredients and auxiliary substances are used in the agents according to the invention preferably in amounts of 0.0001 to 10 wt % each, particularly 0.0005 to 5 wt %, with respect the total weight of the application mixture.

For intense lightening of very dark hair, the sole use of hydrogen peroxide or the addition products thereof to organic or inorganic compounds is often insufficient. Therefore, the agents according to the invention can additionally include further bleaching agents.

If intense lightening is desired in addition to the coloring of the keratin fiber, it is therefore preferred according to the invention that a bleaching preparation (C), including at least one bleach activator, is additionally added to the mixture of the oxidant preparation (B) and the preparation (A), including at least one oxidation dye intermediate according to formula (I).

It can be irrelevant whether a mixture of (A) and (B) is first produced and the bleaching preparation (C) is then added or whether a sequence of the mixing of the individual components that differs therefrom is used. It is preferred that the individual preparations are mixed as closely as possible in time and the agent ready for use is preferably promptly applied to the keratin fibers.

Therefore, a further embodiment of the present invention is an agent for bleaching and dyeing keratin fibers, characterized in that it is produced before application by mixing at least one oxidant preparation (B), including at least one oxidant, selected from hydrogen peroxide, the addition compounds thereof to solid carriers, at least one bleaching preparation (C), including at least one bleaching-power booster, and at least one preparation (A), including at least one oxidation dye intermediate according to formula (I) in a cosmetic carrier.

In a further embodiment, it is preferred that the dye agent according to the invention additionally includes at least one inorganic peroxo compound as the bleaching preparation (C). The inorganic peroxo compound is preferably selected from ammonium persulfate, alkali metal persulfates, ammonium peroxomonosulfate, alkali metal hydrogen peroxomonosulfates, alkali metal peroxodiphosphates, and alkaline earth metal peroxides. Especially preferred inorganic peroxo compounds as bleaching-power boosters are ammonium peroxodisulfate, potassium peroxodisulfate, sodium peroxodisulfate, potassium hydrogen peroxomonosulfate, potassium peroxodiphosphate, magnesium peroxide, and barium peroxide, particularly ammonium peroxodisulfate, potassium peroxodisulfate, and sodium peroxodisulfate.

The inorganic peroxo compounds are included preferably in an amount of 0.1 to 25 wt %, particularly in an amount of 0.5 to 15 wt %, with respect to the total weight of the agent ready for use.

Persulfate salts or peroxodisulfate salts are used generally in the form of an optionally dedusted powder or a molded body pressed into shape.

However, it can be advantageous according to the invention if the agents are free of inorganic peroxo compounds. However, the agents according to the invention can therefore include a further bleaching-power booster instead of and/or in addition to the solid peroxo compounds.

In the context of this invention, compounds that result in aliphatic peroxocarboxylic acids, such as acylated alkylene diamines, particularly tetraacetylethylenediamine (TAED), and/or substituted perbenzoic acid under perhydrolysis conditions, carbonic acid derivatives, particularly ammonium hydrogen carbonate, ammonium carbonate, sodium hydrogen carbonate, sodium carbonate, potassium hydrogen carbonate, potassium carbonate, and calcium carbonate, alkyl carbonates and carbamates, and silyl carbonates and carbamates can be used as additional bleaching-power boosters.

The bleaching-power boosters used in addition to or instead of peroxo compounds are included in the cosmetic agents according to the invention preferably in amounts of 0.05 to 10 wt %, particularly in amounts of 0.2 to 5 wt %, in each case with respect to the total weight of the agent ready for use.

Although in principle there are no restrictions with regard to the formulation of the bleaching preparation (C), it has proven to be preferred according to the invention that the preparation (C) is formulated water-free.

Within the meaning of the present invention, water-free means a water content with respect to the preparation (C) of less than 5 wt %, particularly of less than 2 wt %. Bleaching preparations that include less than 0.1 wt % of water can be exceptionally preferred according to the invention. The preparation (C) is preferably formulated as a powder or as a water-free paste.

In a further preferred embodiment, the agent can include at least one cationic pyridinium derivative as a bleaching-power booster in the preparation (C). In particular, agents according to the invention that include at least one compound from 2-acetyl-1-methylpyridinium-p-toluenesulfonate and/or 4-acetyl-1-methylpyridinium-p-toluenesulfonate and/or N-methyl-3,4-dihydroisoquinolinium-p-toluenesulfonate as a cationic pyridinium derivative are preferred.

According to an embodiment of the present invention preferred according to the invention, the agent ready for use has a pH between 7 and 11, particularly between 8 and 10.5, particularly preferably between 8.5 and 10.0.

Usually, the pH value is adjusted by means of pH-adjusting agents. Common acidifying and alkalizing agents are familiar to a person skilled in the art of cosmetics for the purpose of adjusting the pH value. The alkalizing agents that can be used to adjust the pH value are typically selected from inorganic salts, particularly of the alkali metals and alkaline earth metals, organic alkalizing agents, particularly amines, basic amino acids and alkanolamines, and ammonia. Acidifying agents preferred according to the invention are edible acids, such as citric acid, acetic acid, malic acid, or tartaric acid, and diluted mineral acids.

The pH values within the meaning of the present invention are pH values that were measured at a temperature of 22° C.

Organic alkalizing agents that can be used according to the invention are preferably selected from alkanolamines from primary, secondary, or tertiary amines having a $C_2$-$C_6$ alkyl skeleton that bears at least one hydroxyl group. Especially preferred alkanolamines are selected from the group comprising 2-aminoethan-1-ol (monoethanolamine), 2-amino-2-methylpropan-1-ol, 2-amino-2-methylpropan-1,3-diol, and triethanolamine.

However, in examinations for the present invention, it emerged that agents also preferred according to the invention are characterized in that they additionally include an inorganic alkalizing agent. The inorganic alkalizing agent according to the invention is preferably selected from the group comprising sodium hydroxide, potassium hydroxide, calcium hydroxide, barium hydroxide, sodium phosphate, potassium phosphate, sodium silicate, potassium silicate, sodium carbonate, and potassium carbonate. Exceptionally preferred are sodium hydroxide and/or potassium hydroxide.

The basic amino acids that can be used as alkalizing agents according to the invention are preferably selected from the group comprising L-arginine, D-arginine, D/L-arginine, L-lysine, D-lysine, D/L-lysine; L-arginine, D-arginine, D/L-arginine are especially preferably used as an alkalizing agent within the meaning of the invention.

Finally, a further preferred alkalizing agent is ammonia.

The alkalizing agents are preferably included in an amount of 0.05 to 10 wt %, particularly 0.5 to 5 wt %, in each case with respect to the total weight of the agent ready for use.

As already mentioned, the agents according to the invention can also be produced immediately before application from two or more preparations packaged separately. This lends itself particularly to separating incompatible ingredients in order to avoid a premature reaction. Separation into multi-component systems is advantageous particularly if incompatibilities of the ingredients are expected or feared. In such systems, the agent ready for use is produced by the consumer immediately before application by mixing the components. A dye agent and/or lightening agent in which the oxidation dye intermediates are initially separated from the oxidant preparation containing preferably hydrogen peroxide is preferred.

A preferred administration form of the agent according to the invention is a packaging unit (kit of parts) that includes, in containers prepared separately from each other, at least one preparation (A), which includes at least one oxidation dye intermediate according to formula (I) in a cosmetic carrier, in a container A, and at least one oxidant preparation (B), which includes at least one oxidant in a cosmetic carrier, in a container B.

If an especially intense lightening effect is desired, a preferred further administration form of the agent according to the invention is a packaging unit (kit of parts) that includes, in containers prepared separately from each other, at least one preparation (A), which includes at least one oxidation dye intermediate according to formula (I) in a cosmetic carrier, in a container A, at least one oxidant preparation (B), which includes at least one oxidant, in a container B, and at least one bleaching preparation (C), which includes at least one bleaching-power booster, in a container C.

The multi-component packaging unit (kit of parts) preferably additionally contains directions. Furthermore, it can be preferred that an application aid, such as a comb or a brush, and/or personal protective equipment, such as disposable gloves, is also included in the kit.

What was said about the agents according to the invention applies, mutatis mutandis, to further preferred embodiments of the multi-component packaging unit (kit of parts).

The actual hair dye agent is expediently produced immediately before application by mixing the preparations (A) and (B) and optionally (C). The application temperatures can lie in a range between 15 and 40° C. After an exposure time of 5 to 45 minutes, the hair dye agent is removed from the hair to be dyed by rinsing the hair dye agent out. If a heavily surfactant-containing carrier, e.g., a dyeing shampoo, was used, post-washing with a shampoo is unnecessary.

During the exposure time of the agent on the fiber, it can be advantageous to support the dyeing process by supplying heat. Heat can be supplied by means of an external heat source, such as hot air from a hot air blower, and, in particular for hair dyeing on a living test subject, by means of the body temperature of the test subject. In the case of the last possibility, the section to be dyed is usually covered with a hood. In particular, the temperature lies between 10° C. and 45° C., particularly between 20° C. and 40° C., during the exposure time. The dye agents according to the invention already result in intense colorings at physiologically acceptable temperatures below 45° C. Therefore, they are suited especially to dyeing human hair.

Further subject matter of the present invention is the use of an agent according to the invention in dye agents for human hair to improve the gray coverage, the levelling, the color intensity, the permanence, and/or the colorfulness of the dyeing results.

What was said about the agents according to the invention applies, mutatis mutandis, to further preferred embodiments of the methods and uses according to the invention.

Finally, further subject matter of the present invention relates to compounds according to formula (I) of the first subject matter of the invention. What was said about the agents according to the invention applies, mutatis mutandis, to further preferred embodiments of these compounds.

EXAMPLES

1) Synthesis Examples a) 2-[(2,5,6-triaminopyrimidin-4-yl)oxy]ethanol, dihydrochloride (i) Synthesis of 2-[(2,6-diaminopyrimidin-4-yl)oxy]ethan-1-ol

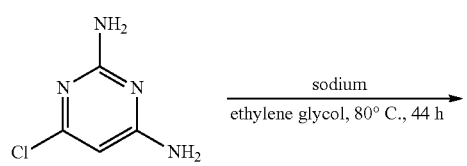

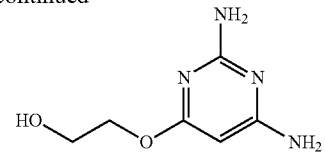

28.9 g (0.20 mol) of 2,4-diamino-6-chloropyrimidine was added to a solution of 4.6 g (0.20 mol) of sodium in 124 ml of ethylene glycol and heated to 80° C. for 44 h while stirring was performed. After termination of the reaction, the solution was diluted with 300 ml of water and extracted with tert-butyl methyl ether (5×200 ml). The combined organic phases were discarded; a precipitate precipitated out of the aqueous phases. The precipitate was washed with water; after drying, 2-[(2,6-diaminopyrimidin-4-yl)oxy]ethan-1-ol (16.1 g, 47%) was obtained as a light-beige solid.

Melting point: 196-199° C.

$^1$H NMR (300 MHz, DMSO-d$_6$): δ=3.61 (t, 2H, 2'-H$_2$), 4.09 (t, 2H, 1'-H$_2$), 5.05 (s, 1H, 5-H), 5.88 (s, 2H, NH$_2$), 6.03 (s, 2H, NH$_2$).

$^{13}$C NMR (125 MHz, DMSO-d$_6$): δ=58.6 (2'-C), 65.6 (1'-C), 75.3 (5-C), 161.9 (2-C), 165.0 (4-C), 169.1 (6-C).

(ii) Synthesis of 2-[(2,6-diamino-5-nitrosopyrimidin-4-yl)oxy]ethan-1-ol

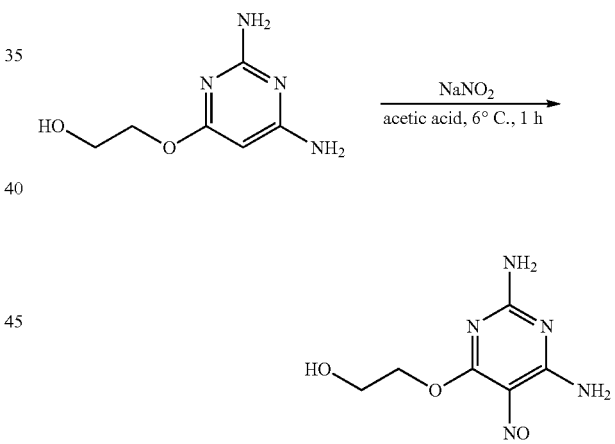

A solution of 4.55 g (0.066 mol) of sodium nitrite in 20 ml of water was added in drops to a solution of 8.50 g (0.050 mol) of 2-[(2,6-diaminopyrimidin-4-yl)oxy]ethan-1-ol in 100 ml of acetic acid (10% in water) over 1 h at 3-5° C. while stirring was performed. Then stirring was performed further for 2 h at room temperature. The resulting precipitate was sucked off, post-washed with water, and dried, whereby 2-[(2,6-diamino-5-nitrosopyrimidin-4-yl)oxy]ethan-1-ol (6.71 g, 67%) was obtained as a purple solid.

Melting point: 260° C. (decomposition)

$^1$H NMR (300 MHz, DMSO-d$_6$): δ=3.80 (t, 2H, 2'-H$_2$), 4.53 (t, 2H, 1'-H$_2$), 7.68 (s, 1H, NH$_2$), 7.75 (s, 1H, NH$_2$), 8.04 (s, 1H, NH$_2$), 10.13 (s, 1H, NH$_2$).

$^{13}$C NMR (125 MHz, DMSO-d$_6$): δ=59.3 (2'-C), 68.7 (1'-C), 139.6 (5-C), 151.0 (2-C), 163.6 (4-C), 171.0 (6-C).

(iii) Synthesis of 2-[(2,5,6-triaminopyrimidin-4-yl)oxy]ethanol, dihydrochloride

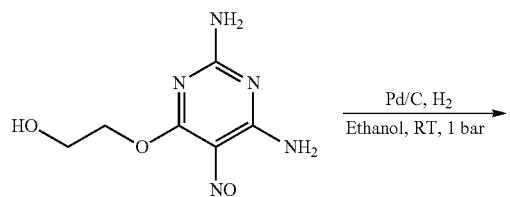

1.5 g (0.04 mol %) of palladium on carbon (5%) was added to a solution of 6.57 g (0.033 mol) of 2-[(2,6-diamino-5-nitrosopyrimidin-4-yl)oxy]ethan-1-ol from step 4.2 in 400 ml of ethanol, and shaking was performed at room temperature for 19 h under hydrogen-1 atmosphere. Then the reaction mixture was poured into 150 ml of diluted hydrochloric acid (0.30 mol), the catalyst was filtered off, and the filtrate was concentrated almost to dryness. The precipitated crystals were sucked off and post-washed with tert-butyl methyl ether. 2-[(2,5,6-triaminopyrimidin-4-yl)oxy]ethanol, dihydrochloride (7.17 g, 84%) was obtained as light-yellow crystals.

Melting point: 176° C. (decomposition)

$^1$H NMR (300 MHz, D$_2$O): δ=3.91 (t, 2H, 2'-H$_2$), 4.54 (t, 2H, 1'-H$_2$).

$^{13}$C NMR (125 MHz, D$_2$O): δ=62.5 (2'-C), 72.8 (1'-C), 87.2 (5-C), 153.9 (2-C), 157.0 (4-C), 168.3 (6-C).

b) 6-[2-(2-methoxyethoxy)ethoxy]pyrimidine-2,4,5-triamine, dihydrochloride

(i) Synthesis of 6-[2-(2-methoxyethoxy)ethoxy]pyrimidine-2,4-diamine

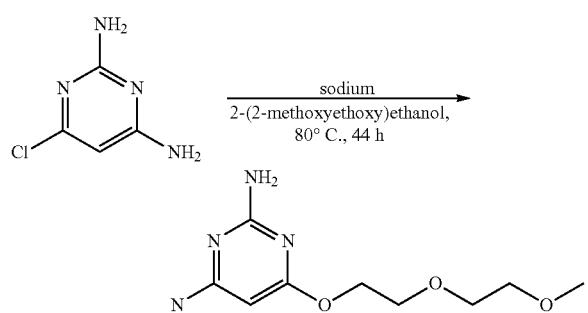

28.9 g (0.20 mol) of 2,4-diamino-6-chloropyrimidine was added to a solution of 4.6 g (0.20 mol) of sodium in 178 ml of 2-(2-methoxyethoxyl)ethanol and heated to 80° C. for 48 h while stirring was performed. After termination of the reaction, the precipitated NaCl was separated and the solution was concentrated to dryness. The residue was taken in ethanol multiple times and concentrated again in order to remove remaining 2-(2-methoxyethoxyl)ethanol. After drying, 6-[2-(2-methoxyethoxyl)ethoxy]pyrimidine-2,4-diamine (49.8 g, 109%) was obtained as brown oil, which still contained 2-(2-methoxyethoxyl)ethanol as a contaminant.

$^1$H NMR (300 MHz, DMSO-d$_6$): δ=3.20 (s, 3H, 5'-H$_3$), 3.26-3.58 (m, 4H, 3'-H$_2$, 4'-H$_2$), 3.62 (t, 2H, 2'-H$_2$), 5.07 (s, 1H, 5-H), 5.90 (s, 2H, NH$_2$), 6.01 (s, 2H, NH$_2$).

$^{13}$C NMR (125 MHz, DMSO-d$_6$): δ=56.4 (5'-C), 69.2 (4'-C), 70.0 (3'-C), 71.6 (2'-C), 72.6 (1'-C), 76.6 (5-C), 163.2 (2-C), 166.3 (4-C), 170.2 (6-C).

(ii) Synthesis of 6-[2-(2-methoxyethoxyl)ethoxy]-5-nitrosopyrimidine-2,4-diamine

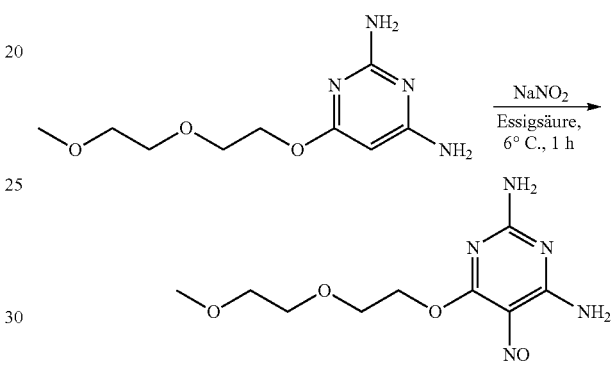

A solution of 9.11 g (0.013 mol) of sodium nitrite in 40 ml of water was added in drops to a solution of 22.8 g (0.100 mol) of 6-[2-(2-methoxyethoxyl)ethoxy]pyrimidine-2,4-diamine in 200 ml of acetic acid (10% in water) over 1 h at 3-5° C. while stirring was performed. Then stirring was performed further for 2 h at room temperature. The resulting precipitate was sucked off, post-washed with water, and dried, whereby 6-[2-(2-methoxyethoxyl)ethoxy]-5-nitrosopyrimidine-2,4-diamine (11.7 g, 45%) was obtained as a purple solid.

Melting point: 163-168° C. (decomposition)

$^1$H NMR (300 MHz, DMSO-d$_6$): δ=3.26 (s, 3H, 5'-H$_3$), 3.50 (t, 2H, 4'-H$_2$), 3.64 (t, 2H, 3'-H$_2$), 3.86 (t, 2H, 2'-H$_2$), 4.66 (t, 2H, 1'-H$_2$), 7.80 (s, 1H, NH$_2$), 7.85 (s, 1H, NH$_2$), 8.09 (s, 1H, NH$_2$), 10.11 (s, 1H, NH$_2$).

$^{13}$C NMR (125 MHz, DMSO-d$_6$): δ=57.1 (5'-C), 65.1 (4'-C), 67.5 (3'-C), 68.8 (2'-C), 70.3 (1'-C), 138.5 (5-C), 149.9 (2-C), 162.4 (4-C), 169.8 (6-C).

(iii) Synthesis of 6-[2-(2-methoxyethoxyl)ethoxy]pyrimidine-2,4,5-triamine, dihydrochloride

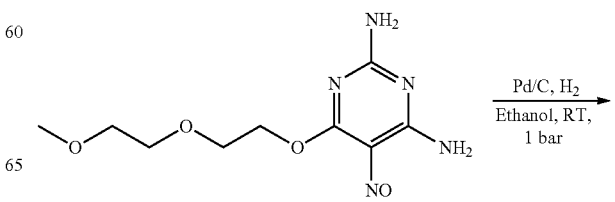

-continued

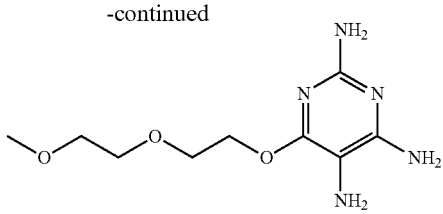

1.5 g (0.04 mol %) of palladium on carbon (5%) was added to a solution of 11.3 g (0.044 mol) of 6-[2-(2-methoxyethoxyl)ethoxy]-5-nitrosopyrimidine-2,4-diamine from step 5.2 in 400 ml of ethanol, and shaking was performed at room temperature for 16 h under hydrogen-1 atmosphere. Then the reaction mixture was poured into 80 ml of diluted hydrochloric acid (0.23 mol), the catalyst was filtered off, and the filtrate was concentrated almost to dryness. The precipitated crystals were sucked off and post-washed with ethanol. 6-[2-(2-methoxyethoxyl)ethoxy]pyrimidine-2,4,5-triamine, dihydrochloride (11.7 g, 84%) was obtained as white crystals.

Melting point: 177-180° C.

$^1$H NMR (300 MHz, CDCl$_3$): δ=0.73 (s, 3H, 5'-H$_3$), 1.00 (t, 2H, 4'-H$_2$), 1.10 (t, 2H, 3'-H$_2$), 1.26 (t, 2H, 2'-H$_2$), 1.97 (t, 2H, 1'-H$_2$).

$^{13}$C NMR (125 MHz, CDCl$_3$): δ=66.0 (5'-C), 66.1 (4'-C), 66.8 (3'-C), 67.7 (2'-C), 69.3 (1'-C), 82.6 (5-C), 149.9 (2-C), 152.1 (4-C), 163.6 (6-C).

2) Colorations

Production of the Dyeing Cream

A dyeing cream of the following composition was produced:

| | | |
|---|---|---|
| Hydrenol ® D[1] | 8.5 wt % | |
| Lorol ® tech.[2] | 2.0 wt % | |
| Texapon ® NSO[3] | 20.0 wt % | |
| Dehyton ® K[4] | 12.5 wt % | |
| Eumulgin ® B2[5] | 0.75 wt % | |
| Sodium sulfite | 1.0 wt % | |
| Ammonium sulfate | 1.0 wt % | |
| Developer component | 3 mmol | |
| Coupler component | 3 mmol | |
| Water | ad 100 | |

[1]C$_{16-18}$ fatty alcohol (INCI designation: Cetearyl Alcohol) (Cognis)
[2]C$_{12-18}$ fatty alcohol (INCI designation: Coconut Alcohol) (Cognis)
[3]Lauryl ether sulfate, sodium salt (approx. 27.5% active substance; INCI designation: Sodium Laureth Sulfate) (Cognis)
[4]N,N-dimethyl-N-(C$_{12-18}$ cocamidopropyl)ammonium acetobetaine (approx. 30% active substance; INCI designation: Aqua (Water), Cocamidopropyl Betaine) (Cognis)
[5]Cetylstearyl alcohol having approx. 20 EO units (INCI designation: Ceteareth-20) (Cognis)

Hydrenol D and Lorol tech. were melted together with Texapon NSO, Dehyton K, and Eumulgin B2 at 80° C. Then the melt was emulsified with the sodium sulfite and ammonium sulfate dissolved in a part of the water. The developer according to the invention was dissolved in a further part of the indicated water amount while heating was performed and was added while stirring was performed. The coupler was likewise dissolved in a part of the indicated water amount and was added while stirring was performed. Then the formulation was filled to 100% with water and stirred cold.

The dyeing cream obtained in this way was mixed at a ratio of 1:1 with the following developer dispersion having a hydrogen peroxide content of 6%.

| | |
|---|---|
| Dipicolinic acid | 0.1 wt % |
| Sodium pyrophosphate | 0.03 wt % |
| Turpinal ® SL[6] | 1.50 wt % |
| Texapon ® N28[7] | 2.00 wt % |
| Acrysol ® 22[8] | 0.60 wt % |
| Hydrogen peroxide, 50% | 6.00 wt % |
| Sodium hydroxide solution, 45% | 0.80 wt % |
| Water | ad 100 wt % |

[6]1-Hydroxyethane-1,1-diphosphonic acid (approx. 58-61% active substance content; INCI designation: Etidronic Acid, Aqua (Water)) (Solutia)
[7]Lauryl ether sulfate sodium salt (at least 26.5% active substance content; INCI designation: Sodium Laureth Sulfate) (Cognis)
[8]Acrylic polymer (approx. 29.5-30.5% solids in water; INCI designation: Acrylates/Steareth-20 Methacrylate Copolymer)

For the dyeing process, four amounts of the mixture ready for use were each applied to a strand of hair that was 80% gray (Kerling). After an exposure time of 30 minutes at 32° C., the strands were rinsed out and washed out with a common shampoo. The coloring of the strands was visually evaluated under the daylight lamp after drying. The dyeing results are summarized in the following table.

a) Colorations by means of
2-[(2,5,6-triaminopyrimidin-4-yl)oxy]ethanol, dihydrochloride

| Example | Coupler component | Obtained nuance/color intensity |
|---|---|---|
| 1 | resorcinol | Pompeian red/+++ |
| 2 | 3-amino-2-methylamino-6-methoxypyridine | beaver brown/+++ |
| 3 | 5-amino-2-methylphenol | violet brown/++ |
| 4 | 3-amino-2-hydroxypyridine | clay-colored/+ |
| 5 | 1,3-bis(2,4-diaminophenoxy)propane | dark blue/+++ |
| 6 | 2,7-dihydroxynaphthalene | caramel brown/+ |
| 7 | 2-methylresorcinol | cherry red/+++ |

+++high intensity
++medium intensity
+low intensity b) Colorations by means of 6-[2-(2-methoxyethoxyl)ethoxy]pyrimidine-2,4,5-triamine, dihydrochloride

| Example | Coupler component | Obtained nuance/color intensity |
|---|---|---|
| 1 | resorcinol | bronze red/+++ |
| 2 | 3-amino-2-methylamino-6-methoxypyridine | olive brown/+++ |
| 3 | 5-amino-2-methylphenol | gray red/++ |
| 4 | 3-amino-2-hydroxypyridine | golden blonde/+ |
| 5 | 1,3-bis(2,4-diaminophenoxy)propane | blue gray/+++ |
| 6 | 2,7-dihydroxynaphthalene | brown orange/+ |
| 7 | 2-methylresorcinol | brown red/+++ |

+++high intensity
++medium intensity
+low intensity

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:
1. An agent for dyeing keratin fibers, comprising:
a cosmetic carrier, and
at least one compound of formula (I) and/or one physiologically acceptable salt of a compound of formula (I)

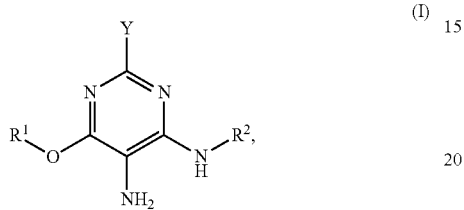

in which
R$^1$, R$^2$ stand, independently of each other, for a hydrogen atom, a C$_1$-C$_8$ alkyl group, a C$_2$-C$_6$ alkenyl group, a C$_1$-C$_6$ hydroxyalkyl group, a C$_2$-C$_8$ polyhydroxyalkyl group, a C$_1$-C$_6$ alkoxy group, a C$_1$-C$_6$ alkoxy C$_1$-C$_6$ hydroxyalkyl group, a C$_1$-C$_6$ alkoxy C$_2$-C$_6$ alkyl group, a C$_1$-C$_6$ polyalkoxy group, an amino C$_2$-C$_6$ alkyl group, wherein the amino group can be substituted with one or two groups X, a C$_1$-C$_6$ alkylamino C$_2$-C$_6$ alkyl group, a C$_1$-C$_6$ alkylamino (C$_1$-C$_6$) alkoxy group, a nitro (C$_1$-C$_6$) alkyl group, a C$_1$-C$_6$ cyanoalkyl group, a C$_1$-C$_6$ alkylamido (C$_1$-C$_6$) alkyl group, wherein the amide function can be substituted with one or two groups X, an aryl group, or a halogen (C$_1$-C$_6$) alkyl group, wherein the halogen can be fluorine, chlorine, bromine, or iodine,
Y stands for an NH$_2$ or OH group,
with the proviso that, if R$^1$ stands for a C$_1$-C$_4$ alkyl group, R$^2$ does not stand for hydrogen, a C$_1$-C$_4$ alkyl group, or an aryl group
wherein the compound of formula (I) is selected from the group consisting of: [(2,5,6-triaminopyrimidin-4-yl)oxy]methanol, [(2,5,6-triaminopyrimidin-4-yl)oxy]ethanol, [(2,5,6-triaminopyrimidin-4-yl)oxy]propanol, 6-(methoxymethoxy)pyrimidine-2,4,5-triamine, 6-(2-methoxyethoxy)pyrimidine-2,4,5-triamine, 6-(3-methoxypropoxy)pyrimidine-2,4,5-triamine, 6-(ethoxymethoxy)pyrimidine-2,4,5-triamine, 6-(2-ethoxyethoxy)pyrimidine-2,4,5-triamine, 6-(3-ethoxypropoxy)pyrimidine-2,4,5-triamine, {[(2,5,6-triaminopyrimidin-4-yl)oxy]methoxy}methanol, {[(2,5,6-triaminopyrimidin-4-yl)oxy]ethoxy}ethanol, {[(2,5,6-triaminopyrimidin-4-yl)oxy]propoxy}propanol, 6-[(methoxymethoxy)methoxy]pyrimidine-2,4,5-triamine, 6-[2-(2-methoxyethoxy)ethoxy]pyrimidine-2,4,5-triamine, 6-[3-(3-methoxypropoxy)propoxy]pyrimidine-2,4,5-triamine, 6-[(ethoxymethoxy)methoxy]pyrimidine-2,4,5-triamine, 6-[2-(2-ethoxyethoxy)ethoxy]pyrimidine-2,4,5-triamine, 6-[3-(3-ethoxypropoxy)propoxy]pyrimidine-2,4,5-triamine, 6-[(methylamino)methoxy]pyrimidine-2,4,5-triamine, 6-[2-(methylamino)ethoxy]pyrimidine-2,4,5-triamine, 6-[3-(methylamino)propoxy]pyrimidine-2,4,5-triamine, 6-[(ethylamino)methoxy]pyrimidine-2,4,5-triamine, 6-[2-(ethylamino)ethoxy]pyrimidine-2,4,5-triamine, 6-[2-(ethylamino)propoxy]pyrimidine-2,4,5-triamine, 6-{[(methoxymethyl)amino]methoxy}pyrimidine-2,4,5-triamine, 6-{2-[(2-(methoxyethyl)amino]ethoxy}pyrimidine-2,4,5-triamine, 6-{3-[(3-methoxypropyl)amino]propoxy}pyrimidine-2,4,5-triamine, 6-phenoxypyrimidine-2,4,5-triamine, 6-(4-methylphenoxy)pyrimidine-2,4,5-triamine, 6-(2-methylphenoxy)pyrimidine-2,4,5-triamine, 6-(3-methylphenoxy)pyrimidine-2,4,5-triamine, 6-benzyloxypyrimidine-2,4,5-triamine, [(2,5-diamino-6-(methylamino)pyrimidin-4-yl)oxy]methanol, 2-{[2,5-diamino-6-(methylamino)pyrimidin-4-yl]oxy}ethanol, [(2,5-diamino-6-(methylamino)pyrimidin-4-yl)oxy]propanol, 6-(methoxymethoxy)-N$^4$-methylpyrimidine-2,4,5-triamine, 6-(2-methoxyethoxy)-N$^4$-methylpyrimidine-2,4,5-triamine, 6-(3-methoxypropoxy)-N$^4$-methylpyrimidine-2,4,5-triamine, 6-(ethoxymethoxy)-N$^4$-methylpyrimidine-2,4,5-triamine, 6-(2-ethoxyethoxy)-N$^4$-methylpyrimidine-2,4,5-triamine, 6-(3-ethoxypropoxy)-N$^4$-methylpyrimidine-2,4,5-triamine, ({[2,5-diamino-6-(methylamino)pyrimidin-4-yl]oxy}methoxy)methanol, 2-(2-{[2,5-diamino-6-(methylamino)pyrimidin-4-yl]oxy}ethoxy)ethanol, 3-(3-{[2,5-diamino-6-(methylamino)pyrimidin-4-yl]oxy}propoxy)propan-1-ol, 6-[(methoxymethoxy)methoxy]-N$^4$-methylpyrimidine-2,4,5-triamine, 6-[2-(2-methoxyethoxy)ethoxy]-N$^4$-methylpyrimidine-2,4,5-triamine, 6-[3-(3-methoxypropoxy)propoxy]-N$^4$-methylpyrimidine-2,4,5-triamine, 6-[(ethoxymethoxy)methoxy]-N$^4$-methylpyrimidine-2,4,5-triamine, 6-[2-(2-ethoxyethoxy)ethoxy]-N$^4$-methylpyrimidine-2,4,5-triamine, 6-[3-(3-ethoxypropoxy)propoxy]-N$^4$-methylpyrimidine-2,4,5-triamine, N$^4$-methyl-6-[(methylamino)methoxy]pyrimidine-2,4,5-triamine, N$^4$-methyl-6-[2-(methylamino)ethoxy]pyrimidine-2,4,5-triamine, N$^4$-methyl-6-[3-(methylamino)propoxy]pyrimidine-2,4,5-triamine, N$^4$-methyl-6-[(ethylamino)methoxy]pyrimidine-2,4,5-triamine, N$^4$-methyl-6-[2-(ethylamino)ethoxy]pyrimidine-2,4,5-triamine, N$^4$-methyl-6-[2-(ethylamino)propoxy]pyrimidine-2,4,5-triamine, 6-{[(methoxymethyl)amino]methoxy}pyrimidine-2,4,5-triamine, 6-{2-[(2-methoxyethyl)amino]ethoxy}-N$^4$-methylpyrimidine-2,4,5-triamine, 6-{[3-(methoxypropyl)amino]propoxy}-N$^4$-methylpyrimidine-2,4,5-triamine, N$^4$-methyl-6-phenoxypyrimidine-2,4,5-triamine, N$^4$-methyl-6-(4-methylphenoxy)pyrimidine-2,4,5-triamine, 6-(benzyloxy)-N$^4$-methylpyrimidine-2,4,5-triamine, 2-{[2,5-diamino-6-(ethylamino)pyrimidin-4-yl]oxy}ethanol, 6-(ethoxymethoxy)-N$^4$-ethylpyrimidine-2,4,5-triamine, 6-[2-(2-methoxyethoxy)ethoxy]-N$^4$-ethylpyrimidine-2,4,5-triamine, 6-[3-(3-methoxypropoxy)propoxy]-N$^4$-ethylpyrimidine-2,4,5-triamine, N$^4$-ethyl-6-[(methylamino)methoxy]pyrimidine-2,4,5-triamine, N$^4$-ethyl-6-[2-(methylamino)ethoxy]pyrimidine-2,4,5-triamine, N$^4$-ethyl-6-phenoxypyrimidine-2,4,5-triamine, 6-(benzyloxy)-N$^4$-ethylpyrimidine-2,4,5-triamine, 2-[(2,5-diamino-6-anilinopyrimidin-4-yl)oxy]ethanol, 6-(ethoxymethoxy)-N$^4$-phenylpyrimidine-2,4,5-triamine, 6-[2-(2-methoxyethoxy)ethoxy]-N$^4$-phenylpyrimidine-2,4,5-triamine, 6-[3-(3-methoxypropoxy)propoxy]-N$^4$-phenylpyrimidine-2,4,5-triamine, 6-[(methylamino)methoxy]-N$^4$-phenylpyrimidine-2,4,5-triamine, 6-[2-(methylamino)ethoxy]-N$^4$-phenylpyrimidine-2,4,5-triamine, 6-phenoxy-N$^4$-phenylpyrimidine-2,4,5-triamine, 6-(benzyloxy)-N$^4$- phenylpyrimidine-2,4,5-triamine, combinations thereof, and the physiologically acceptable salts thereof.

2. The agent according to claim 1, wherein the agent includes 2-[(2,5,6-triaminopyrimidin-4-yl)oxy]ethanol and/or a physiologically acceptable salt thereof.

3. The agent according to claim 1, wherein the agent includes 6-[2-(2-methoxyethoxy)ethoxy]pyrimidine-2,4,5-triamine and/or a physiologically acceptable salt thereof.

4. The agent according to claim 1, wherein the compound of formula (I) and/or the physiologically acceptable salts thereof comprise 0.001 wt % to 5.0 wt % of the total weight of the agent.

5. The agent according to claim 1, wherein the compound of formula (I) and/or the physiologically acceptable salts thereof comprise 0.025 wt % to 2.5 wt % of the total weight of the agent.

6. The agent according to claim 1, further comprising 0.001 to 5.0 wt % of at least one coupler component based on the total weight of the agent.

7. The agent according to claim 6, wherein the at least one coupler comprises 0.025 to 2.5 wt % of the total weight of the agent.

8. The agent according to claim 6, wherein the coupler is includes at least one compound selected from the group consisting of: 1,3-bis-(2,4-diaminophenoxy)propane, m-aminophenol, resorcinol, 5-amino-2-methylphenol, 2-methylresorcinol, 2-chloro-6-methyl-3-aminophenol, 2,7-dihydroxynaphthalene, 4-chlororesorcinol, 2,6-dihydroxy-3,4-dimethylpyridine, 1-methoxy-2-amino-4-β-hydroxyethylamino-benzene (Lehmann's blue), 2,4-diaminophenoxyethanol, 5-amino-4-chloro-o-cresol, 3-amino-6-methoxy-2-methylaminopyridine, 5-amino-4-chloro-o-cresol, and/or a physiologically acceptable salt of these compounds.

9. The agent according to claim 1, wherein the agent includes 2-[(2,5,6-triaminopyrimidin-4-yl)oxy]ethanol and/or one of the physiologically acceptable salts thereof and a coupler selected from the group consisting of 5-amino-2-methylphenol, 1,3-bis(2,4-diaminophenoxy)propane, resorcinol, 2-methylresorcinol, 2-amino-3-hydroxypyridine, 3-amino-2-methylamino-6-methoxypyridine, 2,7-dihydroxynaphthalene, combinations thereof, and the physiologically acceptable salts of these compounds.

10. The agent according to claim 1, wherein the agent includes 6-[2-(2-methoxyethoxy)ethoxy]pyrimidine-2,4,5-triamine and/or one of the physiologically acceptable salts thereof and a coupler selected from the group consisting of 5-amino-2-methylphenol, 1,3-bis(2,4-diaminophenoxy)propane, resorcinol, 2-methylresorcinol, 2-amino-3-hydroxypyridine, 3-amino-2-methylamino-6-methoxypyridine, 2,7-dihydroxynaphthalene, combinations thereof, and the physiologically acceptable salts of these compounds.

11. The agent for dyeing and optionally simultaneously lightening keratin fibers according to claim 1, further comprising 0.5 wt % to 15 wt % of hydrogen peroxide based on the total weight of the agent.

12. The agent for dyeing and optionally simultaneously lightening keratin fibers according to claim 11, wherein the hydrogen peroxide comprises 1.5 wt % to 10 wt % of the agent.

13. A compound according to formula (I) or a physiologically acceptable salt thereof

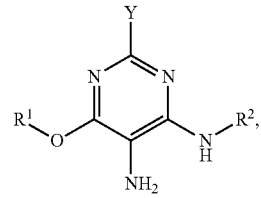

in which
R$^1$, R$^2$ stand, independently of each other, for a hydrogen atom, a C$_1$-C$_8$ alkyl group, a C$_2$-C$_6$ alkenyl group, a C$_1$-C$_6$ hydroxyalkyl group, a C$_2$-C$_8$ polyhydroxyalkyl group, a C$_1$-C$_6$ alkoxy group, a C$_1$-C$_6$ alkoxy C$_1$-C$_6$ hydroxyalkyl group, a C$_1$-C$_6$ alkoxy C$_2$-C$_6$ alkyl group, a C$_1$-C$_6$ polyalkoxy group, an amino C$_2$-C$_6$ alkyl group, wherein the amino group can be substituted with one or two groups X, a C$_1$-C$_6$ alkylamino C$_2$-C$_6$ alkyl group, a C$_1$-C$_6$ alkylamino (C$_1$-C$_6$) alkoxy group, a nitro (C$_1$-C$_6$) alkyl group, a C$_1$-C$_6$ cyanoalkyl group, a C$_1$-C$_6$ alkylamido (C$_1$-C$_6$) alkyl group, wherein the amide function can be substituted with one or two groups X, an aryl group, or a halogen (C$_1$-C$_6$) alkyl group, wherein the halogen can be fluorine, chlorine, bromine, or iodine,
Y stands for an NH$_2$ or OH group,
with the proviso that, if R$^1$ stands for a C$_1$-C$_4$ alkyl group, R$^2$ does not stand for hydrogen, a C$_1$-C$_4$ alkyl group, or an aryl group
wherein the compound of formula (I) is selected from the group consisting of: [(2,5,6-triaminopyrimidin-4-yl)oxy]methanol, [(2,5,6-triaminopyrimidin-4-yl)oxy]ethanol, [(2,5,6-triaminopyrimidin-4-yl)oxy]propanol, 6-(methoxymethoxy)pyrimidine-2,4,5-triamine, 6-(2-methoxyethoxy)pyrimidine-2,4,5-triamine, 6-(3-methoxypropoxy)pyrimidine-2,4,5-triamine, 6-(ethoxymethoxy)pyrimidine-2,4,5-triamine, 6-(2-ethoxyethoxy)pyrimidine-2,4,5-triamine, 6-(3-ethoxypropoxy)pyrimidine-2,4,5-triamine, {[(2,5,6-triaminopyrimidin-4-yl)oxy]methoxy}methanol, {[(2,5,6-triaminopyrimidin-4-yl)oxy]ethoxy}ethanol, {[(2,5,6-triaminopyrimidin-4-yl)oxy]propoxy}propanol, 6-[(methoxymethoxy)methoxy]pyrimidine-2,4,5-triamine, 6-[2-(2-methoxyethoxy)ethoxy]pyrimidine-2,4,5-triamine, 6-[3-(3-methoxypropoxy)propoxy]pyrimidine-2,4,5-triamine, 6-[(ethoxymethoxy)methoxy]pyrimidine-2,4,5-triamine, 6-[2-(2-ethoxyethoxy)ethoxy]pyrimidine-2,4,5-triamine, 6-[3-(3-ethoxypropoxy)propoxy]pyrimidine-2,4,5-triamine, 6-[(methylamino)methoxy]pyrimidine-2,4,5-triamine, 6-[2-(methylamino)ethoxy]pyrimidine-2,4,5-triamine, 6-[3-(methylamino)propoxy]pyrimidine-2,4,5-triamine, 6-[(ethylamino)methoxy]pyrimidine-2,4,5-triamine, 6-[2-(ethylamino)ethoxy]pyrimidine-2,4,5-triamine, 6-[2-(ethylamino)propoxy]pyrimidine-2,4,5-triamine, 6-{[(methoxymethyl)amino]methoxy}pyrimidine-2,4,5-triamine, 6-{2-[(2-(methoxyethyl)amino]ethoxy}pyrimidine-2,4,5-triamine, 6-{3-[(3-(methoxypropyl)amino]propoxy}pyrimidine-2,4,5-triamine, 6-phenoxypyrimidine-2,4,5-triamine, 6-(4-methylphenoxy)pyrimidine-2,4,5-triamine, 6-(2-methylphenoxy)pyrimidine-2,4,5-triamine, 6-(3-methylphenoxy)pyrimidine-2,4,5-triamine, 6-benzyloxypyrimidine-2,4,5- triamine, [(2,5-diamino-6-(methylamino)pyrimidin-4-yl)oxy]methanol, 2-{[2,5-diamino-6-(methylamino)pyrimidin-4-yl]oxy}ethanol, [(2,5-diamino-6-(methylamino)pyrimidin-4-yl)oxy]propanol, 6-(methoxymethoxy)-$N^4$-methylpyrimidine-2,4,5-triamine, 6-(2-methoxyethoxy)-$N^4$-methylpyrimidine-2,4,5-triamine, 6-(3-methoxypropoxy)-$N^4$-methylpyrimidine-2,4,5-triamine, 6-(ethoxymethoxy)-$N^4$-methylpyrimidine-2,4,5-triamine, 6-(2-ethoxyethoxy)-$N^4$-methylpyrimidine-2,4,5-triamine, 6-(3-ethoxypropoxy)-$N^4$-methylpyrimidine-2,4,5-triamine, ({[2,5-diamino-6-(methylamino)pyrimidin-4-yl]oxy}methoxy)methanol, 2-(2-{[2,5-diamino-6-(methylamino)pyrimidin-4-yl]oxy}ethoxy)ethanol, 3-(3-{[2,5-diamino-6-(methylamino)pyrimidin-4-yl]oxy}propoxy)propan-1-ol, 6-[(methoxymethoxy)methoxy]-$N^4$-methylpyrimidine-2,4,5-triamine, 6-[2-(2-methoxyethoxy)ethoxy]-$N^4$-methylpyrimidine-2,4,5-triamine, 6-[3-(3-methoxypropoxy)propoxy]-$N^4$-methylpyrimidine-2,4,5-triamine, 6-[(ethoxymethoxy)methoxy]-$N^4$-methylpyrimidine-2,4,5-triamine, 6-[2-(2-ethoxyethoxy)ethoxy]-$N^4$-methylpyrimidine-2,4,5-triamine, 6-[3-(3-ethoxypropoxy)propoxy]-$N^4$-methylpyrimidine-2,4,5-triamine, $N^4$-methyl-6-[(methylamino)methoxy]pyrimidine-2,4,5-triamine, $N^4$-methyl-6-[2-(methylamino)ethoxy]pyrimidine-2,4,5-triamine, $N^4$-methyl-6-[3-(methylamino)propoxy]pyrimidine-2,4,5-triamine, $N^4$-methyl-6-[(ethylamino)methoxy]pyrimidine-2,4,5-triamine, $N^4$-methyl-6-[2-(ethylamino)ethoxy]pyrimidine-2,4,5-triamine, $N^4$-methyl-6-[2-(ethylamino)propoxy]pyrimidine-2,4,5-triamine, 6-{[methoxymethyl)amino]methoxy}pyrimidine-2,4,5-triamine, 6-{2-[(2-methoxyethyl)amino]ethoxy}-$N^4$-methylpyrimidine-2,4,5-triamine, 6-{[3-(methoxypropyl)amino]propoxy}-$N^4$-methylpyrimidine-2,4,5-triamine, $N^4$-methyl-6-phenoxypyrimidine-2,4,5-triamine, $N^4$-methyl-6-(4-methylphenoxy)pyrimidine-2,4,5-triamine, 6-(benzyloxy)-$N^4$-methylpyrimidine-2,4,5-triamine, 2-{[2,5-diamino-6-(ethylamino)pyrimidin-4-yl]oxy}ethanol, 6-(ethoxymethoxy)-$N^4$-ethylpyrimidine-2,4,5-triamine, 6-[2-(2-methoxyethoxy)ethoxy]-$N^4$-ethylpyrimidine-2,4,5-triamine, 6-[3-(3-methoxypropoxy)propoxy]-$N^4$-ethylpyrimidine-2,4,5-triamine, $N^4$-ethyl-6-[(methylamino)methoxy]pyrimidine-2,4,5-triamine, $N^4$-ethyl-6-[2-(methylamino)ethoxy]pyrimidine-2,4,5-triamine, $N^4$-ethyl-6-phenoxypyrimidine-2,4,5-triamine, 6-(benzyloxy)-$N^4$-ethylpyrimidine-2,4,5-triamine, 2-[(2,5-diamino-6-anilinopyrimidin-4-yl)oxy]ethanol, 6-(ethoxymethoxy)-$N^4$-phenylpyrimidine-2,4,5-triamine, 6-[2-(2-methoxyethoxy)ethoxy]-$N^4$-phenylpyrimidine-2,4,5-triamine, 6-[3-(3-methoxypropoxy)propoxy]-$N^4$-phenylpyrimidine-2,4,5-triamine, 6-[(methylamino)methoxy]-$N^4$-phenylpyrimidine-2,4,5-triamine, 6-[2-(methylamino)ethoxy]-$N^4$-phenylpyrimidine-2,4,5-triamine, 6-phenoxy-$N^4$-phenylpyrimidine-2,4,5-triamine, 6-(benzyloxy)-$N^4$-phenylpyrimidine-2,4,5-triamine, combinations thereof, and the physiologically acceptable salts thereof.

14. The compound of claim 13, the groups $R^1$ and $R^2$ stand, independently of each other, for a hydrogen atom, a $C_1$-$C_6$ alkyl group, an aryl group, a $C_1$-$C_6$ hydroxyalkyl group, a $C_1$-$C_6$ alkoxy group, a $C_1$-$C_6$ alkoxy $C_1$-$C_6$ hydroxyalkyl group, a $C_1$-$C_6$ polyalkoxy group, an amino $C_2$-$C_6$ alkyl group, a $C_1$-$C_6$ alkylamino $C_2$-$C_6$ alkyl group, or a $C_1$-$C_6$ alkylamino ($C_1$-$C_6$) alkoxy group, with the proviso that, if $R^1$ stands for a $C_1$-$C_4$ alkyl group, $R^2$ does not stand for hydrogen, a $C_1$-$C_4$ alkyl group, or an aryl group.

15. The compound of claim 13, wherein the compound is 2-[(2,5,6-triaminopyrimidin-4-yl)oxy]ethanol or a physiologically acceptable salt thereof.

16. The agent according to claim 1, wherein the compound is 6-[2-(2-methoxyethoxy)ethoxy]pyrimidine-2,4,5-triamine or a physiologically acceptable salt thereof.

* * * * *